United States Patent [19]
Sook

[11] Patent Number: 5,331,974
[45] Date of Patent: Jul. 26, 1994

[54] MULTI-PURPOSE SEXUAL DEVICE WITH DISPOSABLE CONDOM USAGE

[76] Inventor: Kim H. Sook, 94-4, Maesanro 3 ga, Kwonseon-ku, Suwon-City, Kyunggi-do, Rep. of Korea

[21] Appl. No.: 4,593

[22] Filed: Jan. 14, 1993

[30] Foreign Application Priority Data

Apr. 16, 1992 [KR] Rep. of Korea ............... 92-6351

[51] Int. Cl.$^5$ .................... A61F 6/02; A61F 6/04
[52] U.S. Cl. .......................... 128/842; 128/844; 128/918
[58] Field of Search ............... 128/842, 844, 918; 604/330, 347–353

[56] References Cited

U.S. PATENT DOCUMENTS

| | | | |
|---|---|---|---|
| 4,805,604 | 2/1989 | Spery | 128/844 |
| 4,808,174 | 2/1989 | Sorkin | 128/844 |
| 4,840,187 | 6/1989 | Brazier | 128/844 |
| 4,867,176 | 9/1989 | Lash | 128/844 |
| 4,964,416 | 10/1990 | Foldesy | 128/844 |
| 5,146,930 | 9/1992 | Richardson | 128/842 |
| 5,168,881 | 12/1992 | Reddy | 128/844 |
| 5,199,444 | 4/1993 | Wheeler | 128/844 |

*Primary Examiner*—Michael A. Brown
*Attorney, Agent, or Firm*—Nixon & Vanderhye

[57] ABSTRACT

This invention relates to a multi-purpose sexual device usable as a condom usage comprising an insertion part, a pressure part and an air hole with two plys of outer and inner sheets sealed in conformance with its sealing line forming air spaces between the outer and inner sheets of insertion part and pressure part by filling with the proper amount of air blown in through the air hole.

15 Claims, 25 Drawing Sheets

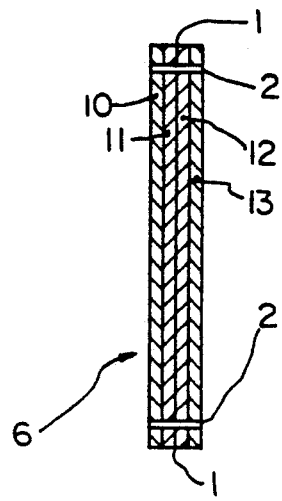
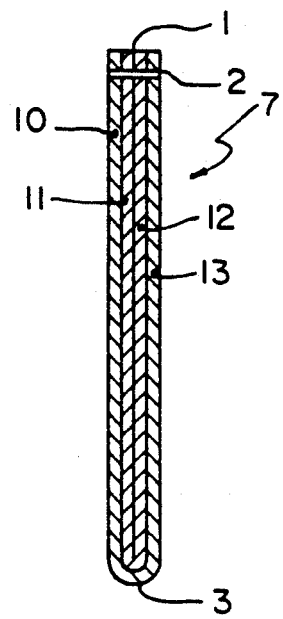
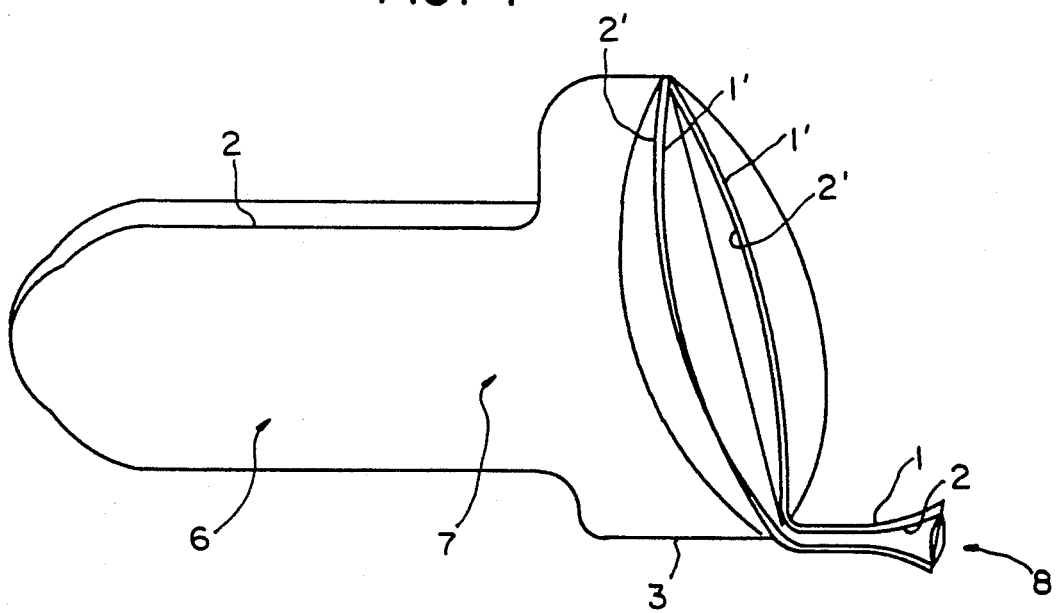

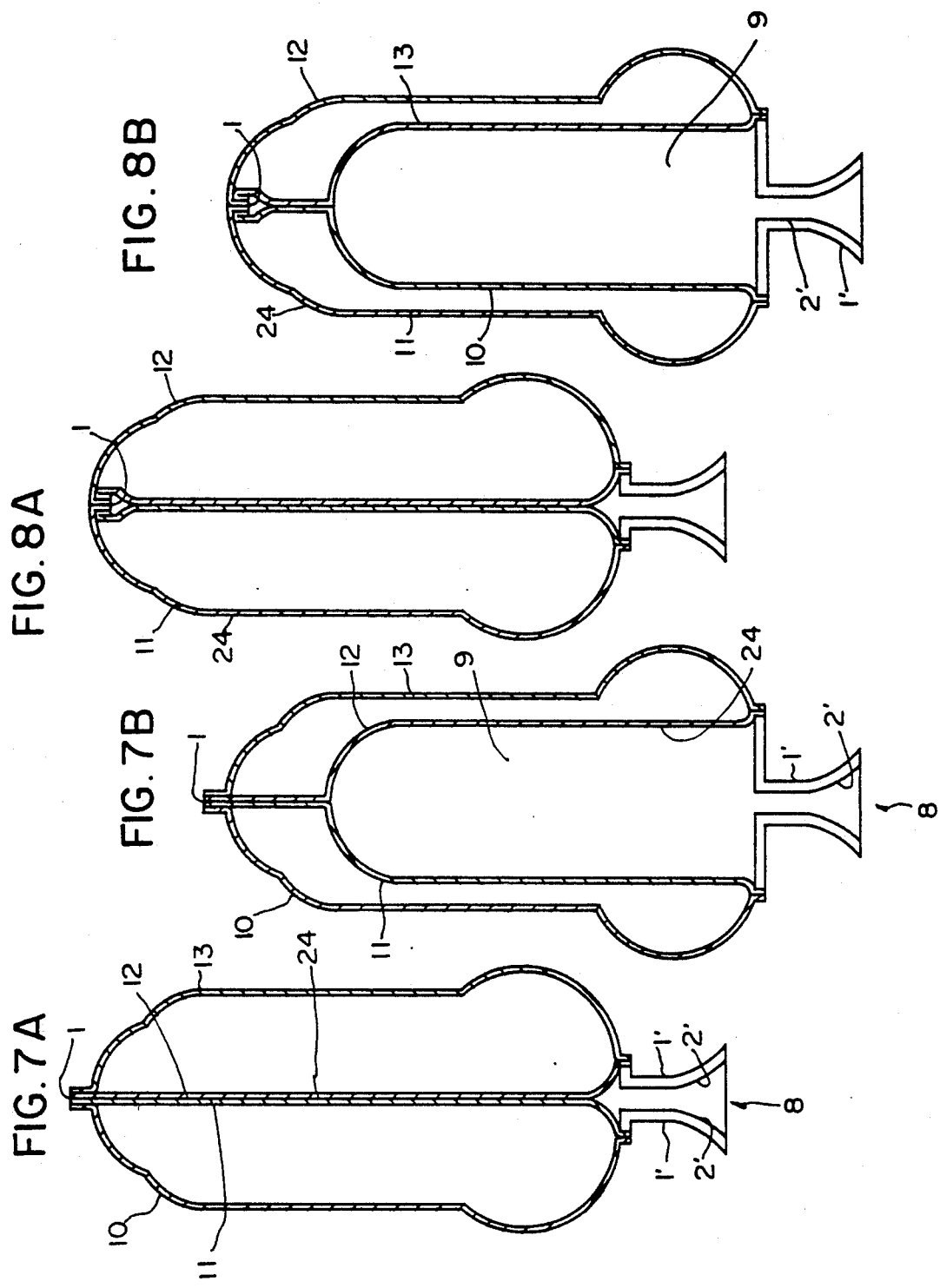

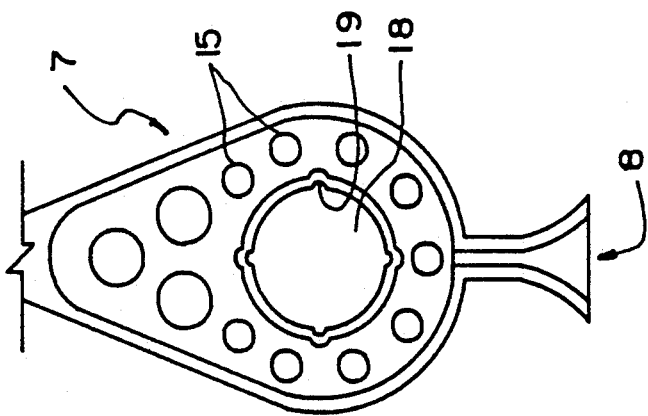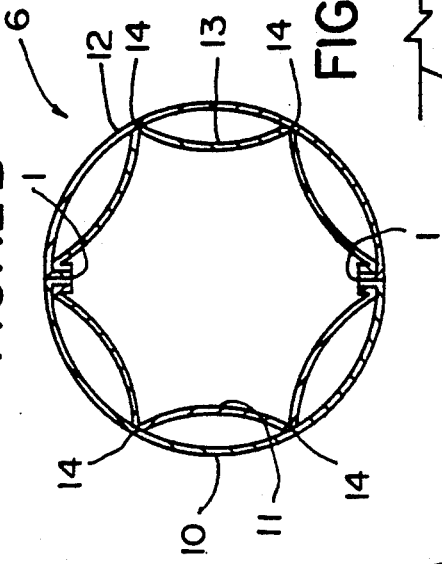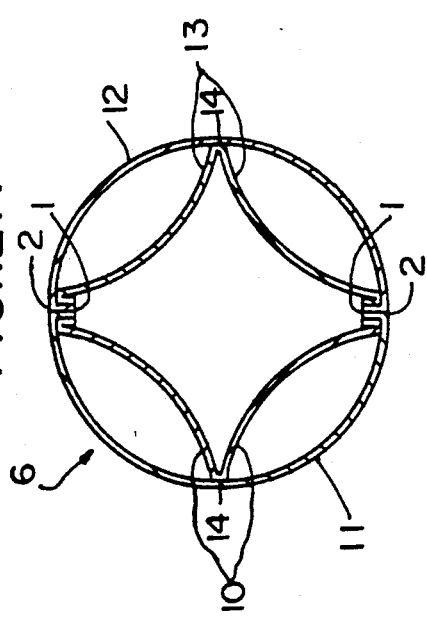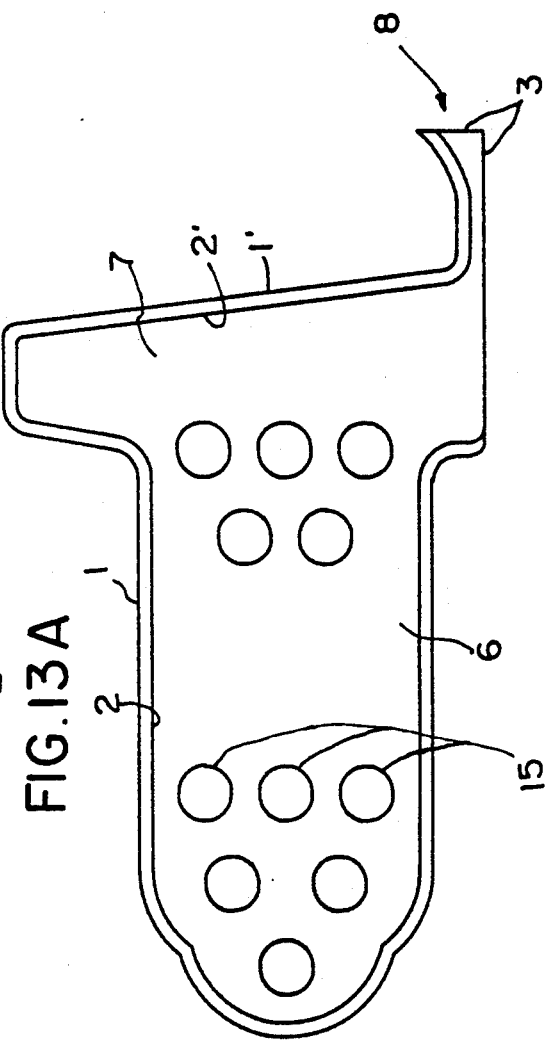

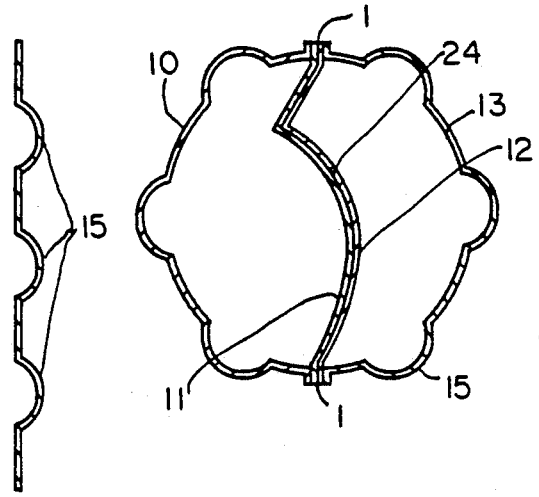
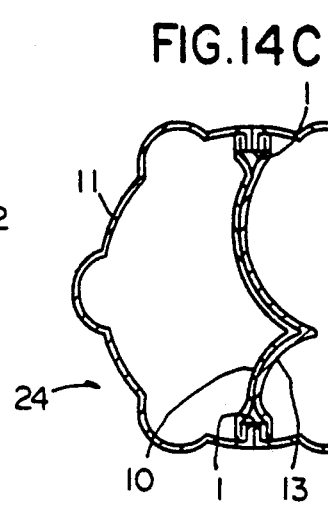
FIG.14A  FIG.14B  FIG.14C
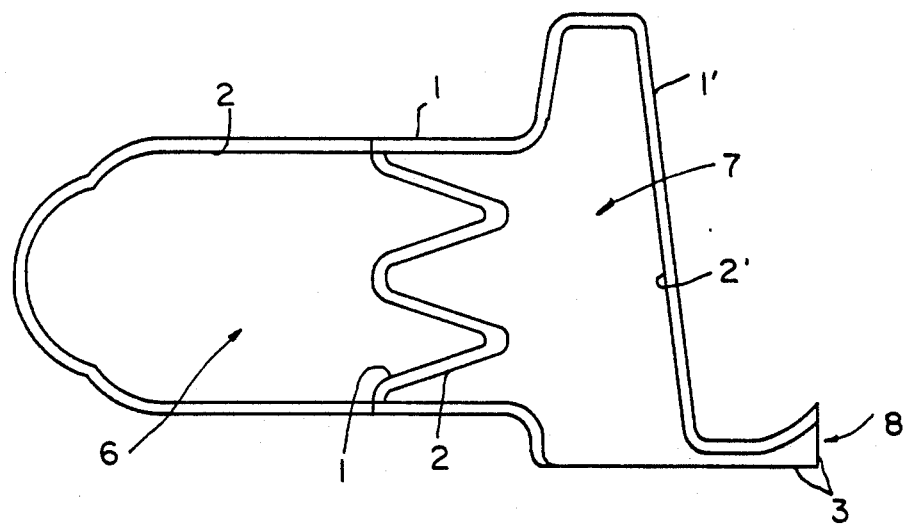
FIG.15

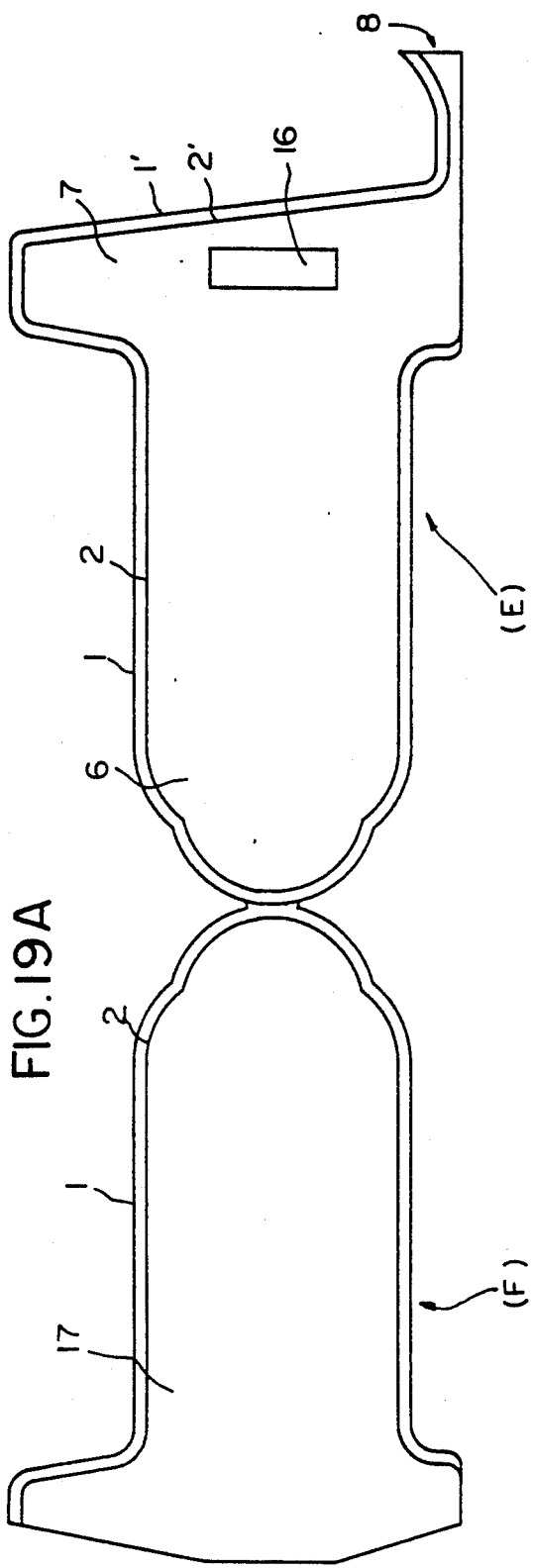
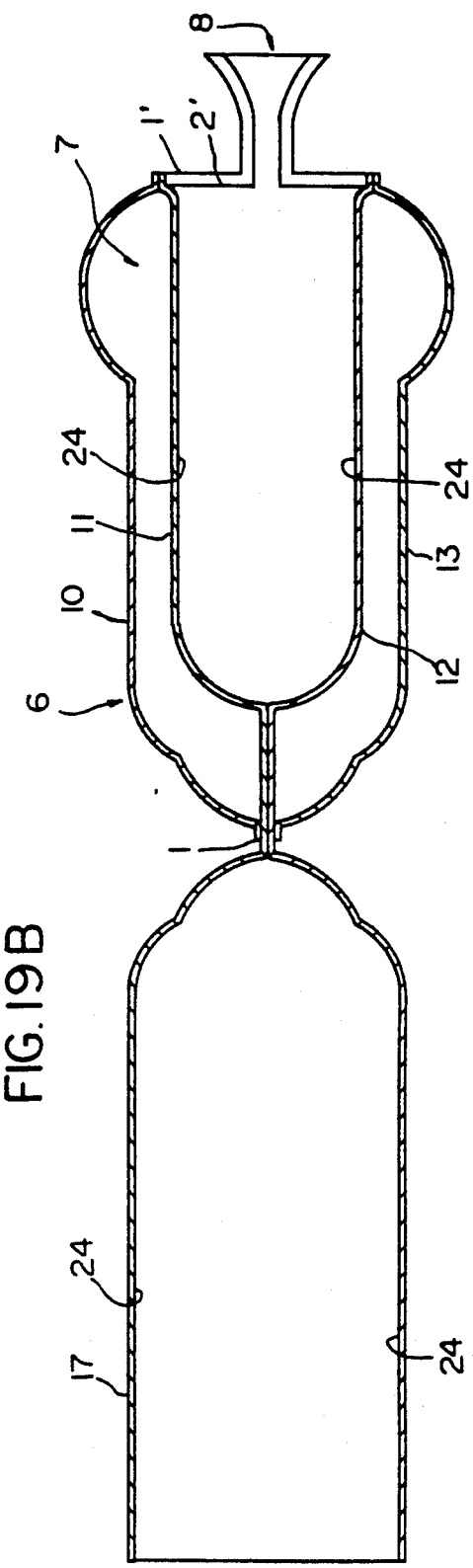
FIG.19A
FIG.19B

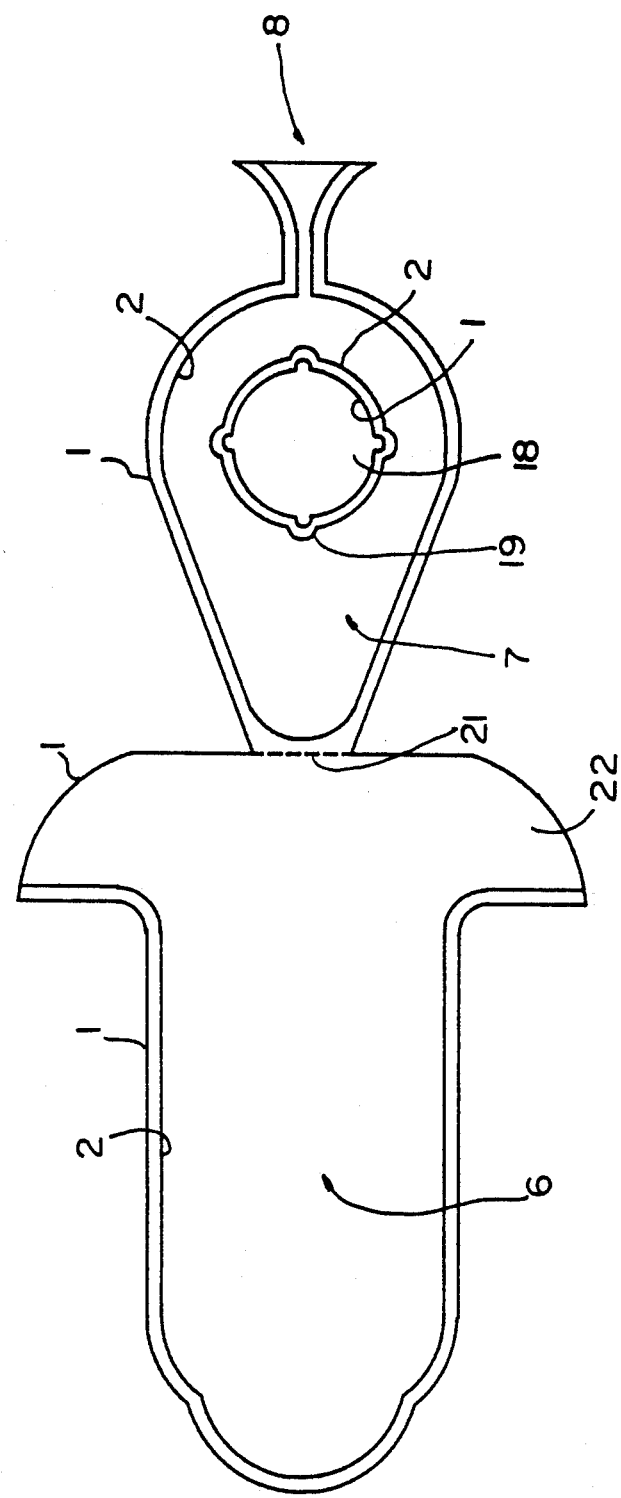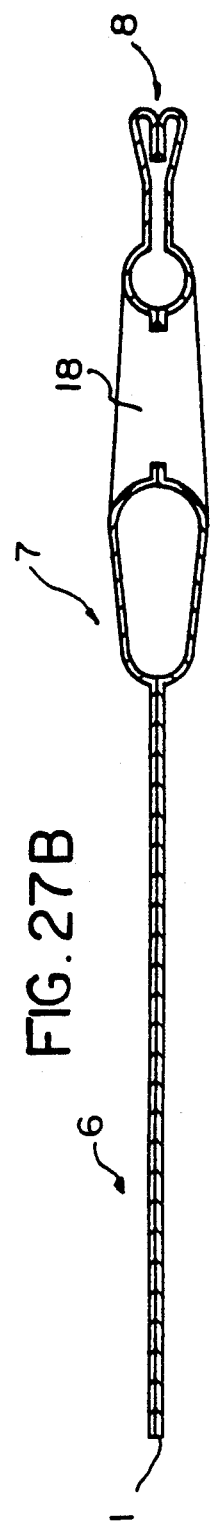
FIG. 27A
FIG. 27B

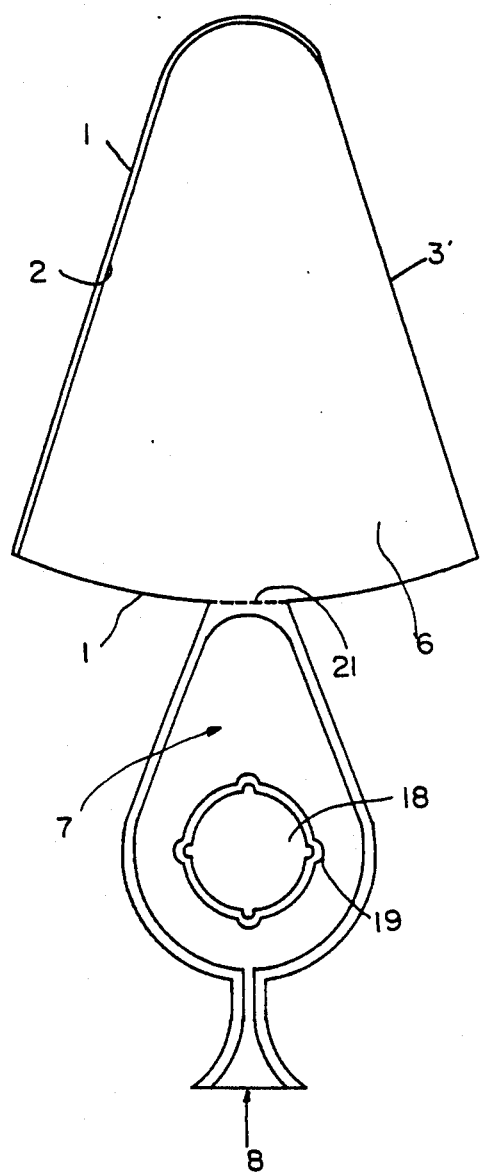
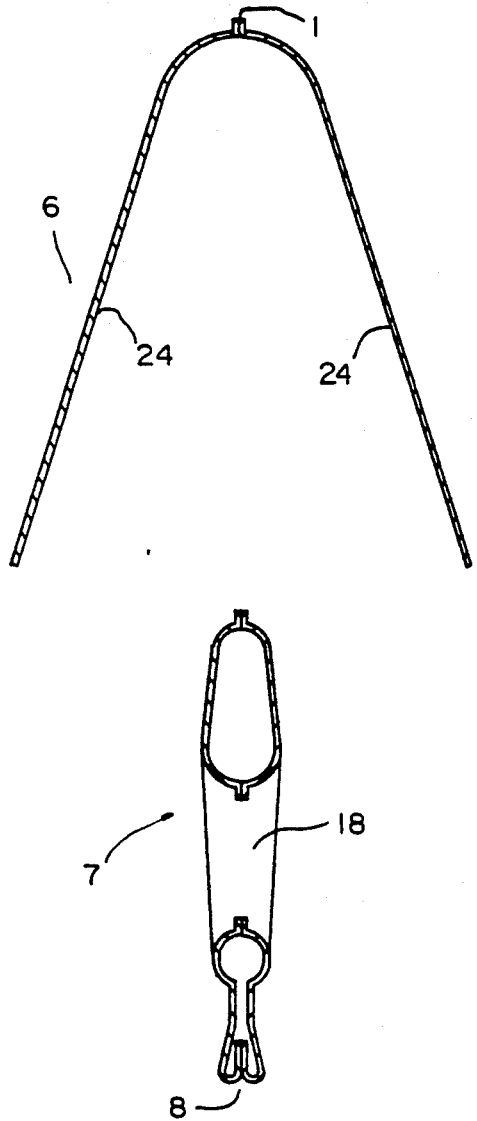

MULTI-PURPOSE SEXUAL DEVICE WITH DISPOSABLE CONDOM USAGE

BACKGROUND OF THE INVENTION

The present invention relates generally to sexual devices and more particularly to a multipurpose sexual device which can be used as a condom.

SUMMARY OF THE INVENTION

This invention relates to a multi-purpose sexual device usable as a condom comprising an insertion part, a pressure part and an air hole with two plys of outer and inner sheets sealed in conformance with its sealing line forming air spaces between the inner and outer sheets of the insertion part and pressure part by filling with the proper amount of air blown in through the air hole. This invention not only has effects of contraception and prevention of venereal disease but helps to solve other sexual problems such as premature ejaculation, insufficient erection and impotence.

BRIEF DESCRIPTION OF THE DRAWINGS

FIG. 2-B is a side elevation view of the completed invention.

FIG. 2-C is a front view showing the reversed state of the present invention.

FIG. 3-A is a cross-sectional view of the insertion part of FIG. 2-B.

FIG. 3-B is a cross-sectional view of the pressure part of FIG. 2-B.

FIG. 4 is a perspective view of the inflated state of the present invention.

FIG. 5-B is a sectional view assuming that a penis is inserted into the state of FIG. 5-A.

FIG. 5-C is a sectional view of the reversed state of FIG. 5-A.

FIG. 5-D is a sectional view assuming that a penis is inserted into the present invention as in FIG. 5-C.

FIG. 6-B is a sectional view showing the state of the present invention as shown in FIG. 6-A assuming that a penis is inserted.

FIG. 6-C is a sectional view of the reversed state of the present invention as in FIG. 6-A.

FIG. 6-D is a section of the present invention assuming that a penis is inserted into the state of FIG. 6-C.

FIG. 7-A is a longitudinal plane sectional view, showing the inflated state of the present invention.

FIG. 7-B is a longitudinal plane sectional view of the present invention assuming that a penis is inserted into the state of FIG. 7-A.

FIG. 8-A is a longitudinal plane sectional view of the present invention assuming that a penis is inserted into the state of FIG. 8-A.

FIG. 10 to FIG. 12 are the embodiments showing the sealing line which forms rugged surface of the present invention by inflating into or isolating from the inside of the sealing line.

FIG. 13 to FIG. 14 are the embodiments showing the prominence and depression forming a certain rugged shape on the surface of the present invention.

FIG. 15 to FIG. 16 are the embodiments of the partially inflated pressure part and insertion part of the present invention.

FIG. 19 to FIG. 21 are the embodiments showing the provision of a cover for use as a condom for male and female in common.

FIG. 27-A to FIG. 27-B are the embodiment of the separate pressure part and insertion part from each other of the present invention.

FIG. 28-A to FIG. 28-B are the embodiment of the present invention featuring a cone shaped hat type insertion part of the present invention.

DESCRIPTION OF THE PREFERRED EMBODIMENTS

Figure 1A:
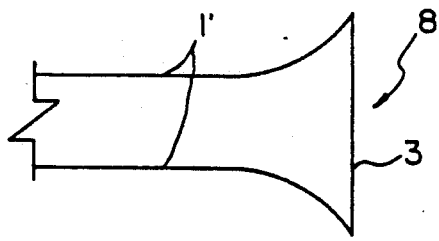
FIG. 1-A to H are an enlarged view of the air chamber of the present invention.
Figure 1C:
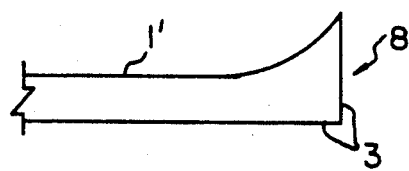
Figure 1B:
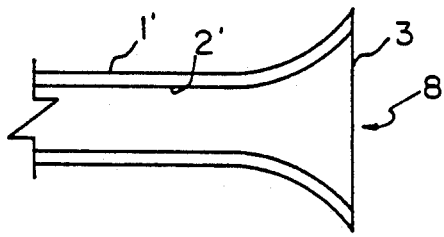
Figure 1D:
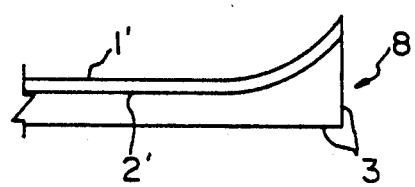
Figure 1E:
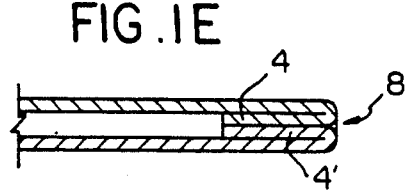
Figure 1F:
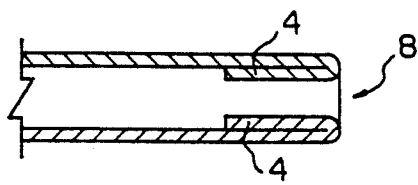
Figure 1H:
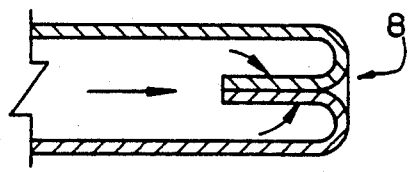
Figure 1G:
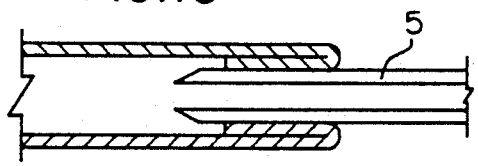

This invention has typical functions such as contraception and prevention of venereal disease as those of general condom and special function for settlement of sexual problems such as premature ejaculation and incomplete election, etc which could not be accomplished by using the general condom.

More specifically, in respect of the materials used for this invention, it made of vinyl which is thin, durable, and harmless materials unlike the typical condom made of latex rubber.

With regard to structure, unlike the general condom comprising simply single ply rubber sheet, this invention consists of three parts such as an insertion part, a pressure part and a multi-functional supporting part;

In accordance with usage or functional effects of each part, the insertion part consists of single-ply or two-plys or three-plys by folding the singly-ply over the two-plys, and the pressure part comprises two or three-plys and the supporting part composes single-ply as well. In these respects, since an air space is formed in all parts of this invention having two-plys, the desired amount of air may be inflated into or deflated from the air space by using mouth or air pump in accordance with usage and structure of each part. Naturally the inflated air cannot be deflated. This point is the gist of this invention.

In relation to production, this invention is manufactured through a very simple procedure by firstly sealing the vinyl sheets in the forms of singly-ply, two-plys or three-plys thereafter and by cutting the sheets in accordance with the sealing lines formed at the time of sealing, leaving an available margin thereof. Accordingly, there is an effect of reduction of cost for installation of manufacturing equipment as well as cost for production. That is, this invention is more economical than the typical condom. Thus, it is possible to produce it in mass scale at an economical expense.

With regard to the operational effect thereof, it also has the added features of overcoming the inevitable phenomena common to the male population such as premature ejaculation, incomplete erection, born small size complex, partial or whole loss of penis by accident, and of using it as an artificial penis or vagina, and of getting perfect sexual satisfaction without worry about infection of venereal disease.

In respect of the way of wearing, the typical condom is put on by unrolling the rolled rubber while this invention can be put on by reversing it on penis or by slidingly inserting penis into the expended entrance part. Accordingly, it is possible to wear this invention more simply than the condom of rolling/unrolling type.

Further, the general condom is coated lubricant on its outer side which contacts with the vagina wall in order for easy insertion of penis into vagina. But, the inner side of condom is stained by the lubricant at rolling time of it for easy wearing on penis, and thus, the condom is easily slipped from the penis. That is, it has a vital weakpoint of high probability of failure of contraception and prevention of venereal disease.

However, in this invention, there is no fear of slipping it from penis since it is put on by reversing or slippingly inserting penis into the side on which any lubricant is coated.

Meanwhile, the reason why a certain amount of necessary margin should be reserved is as follow:

If the sealing and cutting procedures are made in one step for processing convenience, the procedure of production become more simple (in this case, the sealing line is laid on the cutting line.). However, if it is sealed and cut by the heated cut-blade simultaneously, it is concerned that the vinyl sheets are weakly sealed. Accordingly, the probability of failure of contraception and prevention venereal disease become more higher by rupture of the sealed line. Furthermore, the cut line is a rugged shape even if it is infinitely minute, and thus there is danger of making a small hurt on the penis tunic by heavy friction with the cut line when the strong repeat movement is taken place in the state of fastened adhesion.

Therefore, this invention plans to be cut with certain margin after sealing it. In drawings, the margin part is described in the erection stage. However, the vinyl thickness of this invention is about from 0.01 mm to 0.02 mm so that the margin part can fall forward one side even if it is sealed in four plys, in order to prevent penis from accidental hurt due to heavy friction by strong repeat movement in the state of close adhesion.

Further, the probability of rupture of the sealed line is rare although the outer side is ruptured when over-pressure is applied on this invention after air is inflated therein. Also, even if one-ply or two-plys of the four plys are ruptured, there is no danger of failure of contraception or prevention of venereal disease by such a explosion since the explosion is raised in outerside rather than inner side of this invention.

Following are detailed explanation of the attached drawings;

In the drawings, FIG. 1 A-H are shown the air holes of the present invention in which FIG. 1-A is a plane view, FIG. 1-B is other plane view representing a cut-out line (1') and an air-tight sealed line (2'), FIG. 1-C and FIG. 1-D shows the A and B portion of FIG. 1 folded in half in symmetry with the center of the folded line (3), FIG. 1-E is a cross-sectional view of the air hole (8) showing the close adhesion of the open and closed valves (4) (4') to the air hole (8) prior to the blowing-in of air, FIG. 1-F is a sectional view at the time of blowing-in of air with the open and closed valves (4) (4') separated, FIG. 1-G is a sectional view of the nozzle (5) of an air pump inserted into the air hole(8), FIG. 1-H is a sectional view with the mouth removed after blowing air or the nozzle (5) of an air pump taken out and shows the closed state of valves (4) (4') by the inner air pressure represented in arrow eventually blocking any inner air leakage.

Figure 2A:
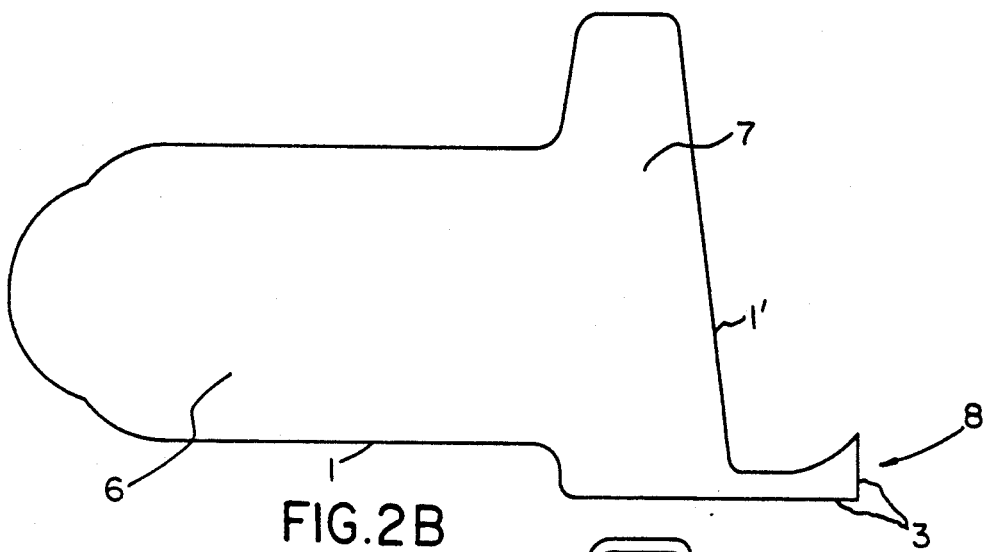
FIG. 2-A is a plan view of the present invention during production.
Figure 2B:
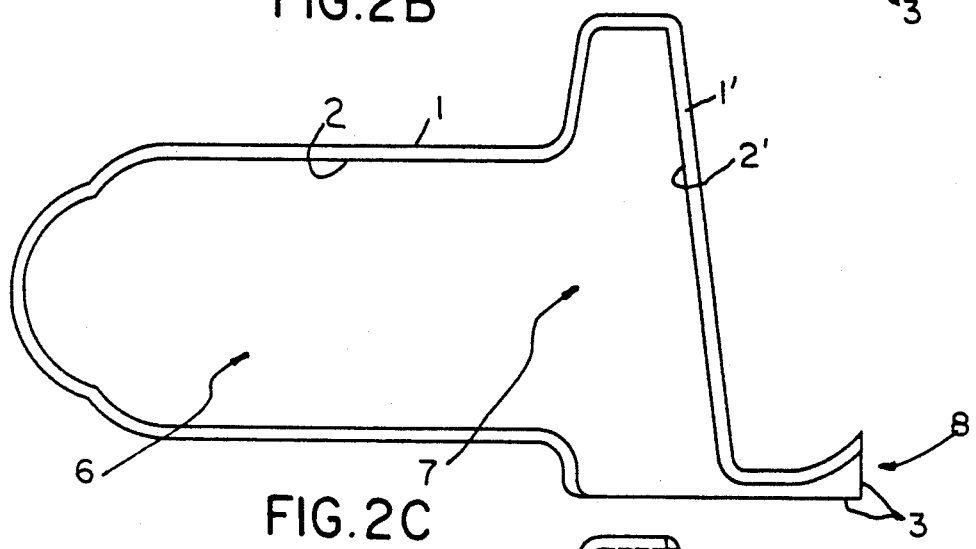
Figure 2C:
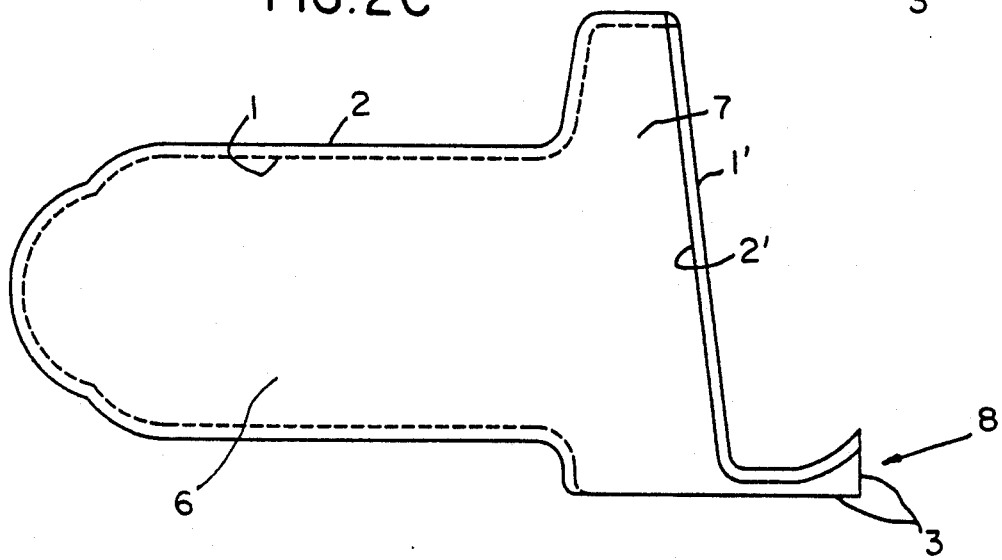
Figure 5A:
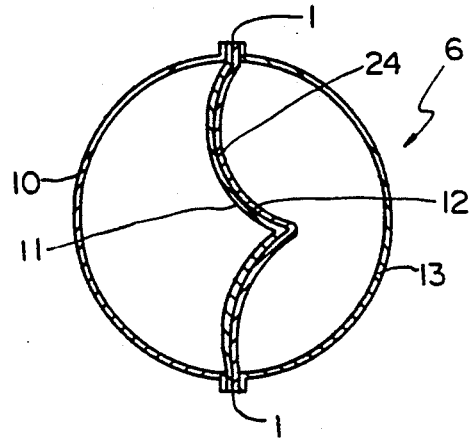
FIG. 5-A is a section view of the insertion part of FIG. 4.
Figure 5B:
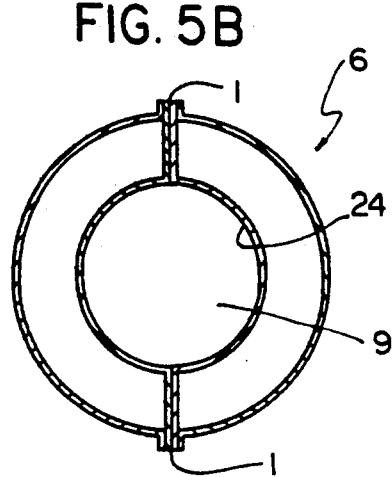
Figure 5C:
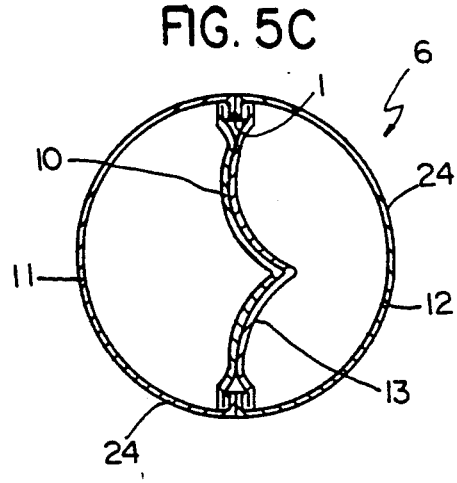
Figure 5D:
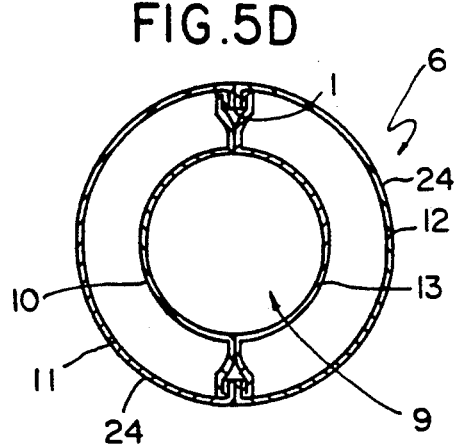
Figure 6A:
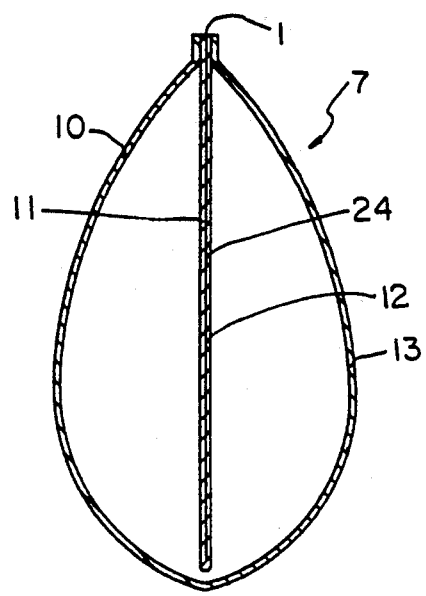
FIG. 6-A is a cross-sectional view of the pressure part of the present invention of FIG. 4.
Figure 6B:
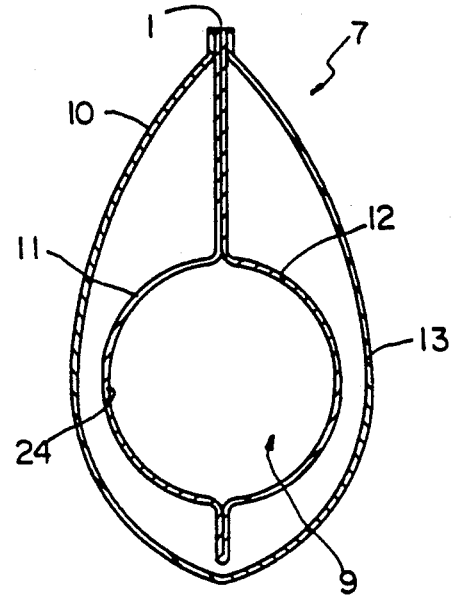
Figure 6C:
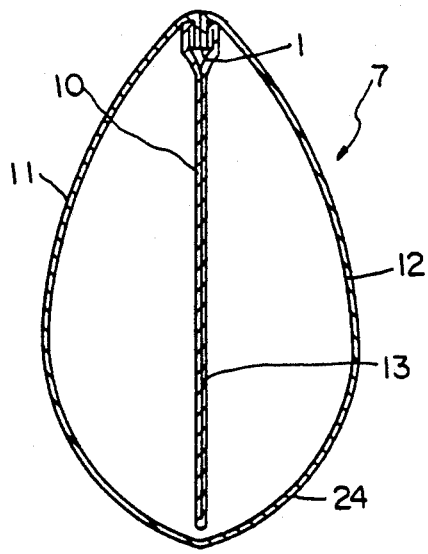
Figure 6D:
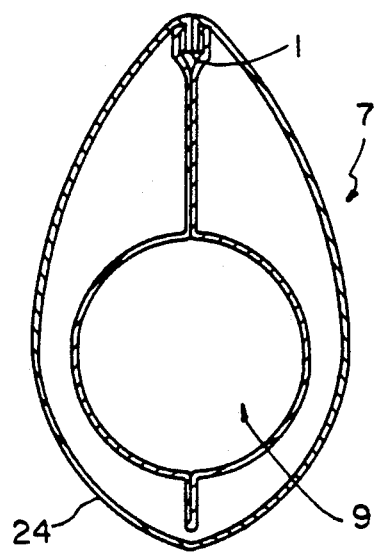

FIG. 2-A,B,C are the plane views of the present invention of which FIG. 2-A is the plane view showing the outside of the present invention prior to the blowing-in of air, FIG. 2-B is the plane view showing the sealed lines (2) (2') not showing in FIG. 2-A with the cut lines (1) (1") and the sealing lines (2) (2') in parallel. FIG. 2-C is the plane view of FIG. 2-B shown inside out with the cut line marked in dotted line and with the sealing line marked in dotted line and with the sealing line marked in a line for representing the outer shape.

However, the cut line (1') and the sealing line (2') of the pressure part of FIG. 2-B and also the folding part (3) will remain as it is represented in FIG. 2-C even though they are reversed inside out.

FIG. 3-A is a longitudinal sectional view of the inserting part (6) of FIG. 2-B, FIG. 3-B comprising 4 plys of vinyl sheets (10) (11) (12) (13), an insertion part (6) has a lower and upper sealing line (2), and pressure part (7) has only one upper sealing line(2) while the lower part has a folding part (3).

FIG. 4 is a perspective view of the present invention expanded by the air through the air hole (8) after reversing the present invention as shown in FIG. 2-C.

FIGS. 5 A-D is a sectional views of the insertion part (6) of FIG. 4 of which two plys (10) (13) out of 4 plys of vinyl sheets (10) (11) (12) (13) make a circle by air pressure and the inner two plys (11) (12) are crumpled irregularly and adhered closely, and FIG. 5-B is a sectional view assuming that the penis(9) is inserted in the artificial vagina as shown in FIG. 5-A.

FIG. 5-C is a sectional view of the insertion part (6) reversed from the state in FIG. 5-A and shows the concealed shape between the vinyl sheets (10) (13) within the circle of the cut line(1) having a certain amount of margin from the sealing line (2) is exposed outside of the circle as shown in FIG. 5-A. FIG. 5-D is a sectional view when assuming that a penis (9) is inserted as shown in FIG. 5-C. Here this section exactly shows the state of sexual relation. In the case of using the present invention as an artificial vagina, a penis is inserted between the vinyl sheets (11) (12) adhered in the center by exposing the cut line (1) to the outside of the circular form without being reversed as shown in FIG. 5-A, in this case, the size of this invention is slightly larger than its basic size in terms of length and width.

The present invention also uses a conventional lubricant for better and safer lubrication between penis and vagina, and the present apparatus.

FIG. 6 A-D is a sectional view of the part corresponding to the pressure part (7) of FIG. 4, and it appears like FIG. 6-A when inflated without reversing, and also has the section of FIG. 6-B when penis is inserted between inner vinyl sheets (11) (12) in order to use this invention as an artificial vagina. FIG. 6-C is a section showing the reversed state of FIG. 6-A. FIG.

6-D is the section of the reversed state of the present invention in FIG. 6-B. Here, the insertion part (6) and the pressure part (7) are formed integrally, inflated simultaneously and coated between the inner vinyl sheets (11) (12) with the lubricant (24). On blowing air, the section of the insertion part (6) is a circle, whereas the section of the pressure part (7) forms the shape of a Rugby oval in which the said pressure part (7) gives better tight rubbing sensation and close fitting sensation around the periphery of vaginal entrance and better constricting sensation to the penis, simultaneously.

Even though someone may have an ideal body constitution, the pubic bones of the male and female seldom offer a satisfactory conjunction put together in terms of an ideal physical insertion and closest contact of both private parts.

Therefore, the pressure parts (7) of the present invention are formed gradually wider toward the bottom part as shown in FIGS. 2-A, B, C. FIG. 7-A is a section showing the longitudinal cutting of the pressure parts inflated without insiding out the present invention. FIG. 7-B is a section showing the insertion of the penis (9) into the above. FIGS. 7-A,B are sections of the present invention used as an artificial vagina. Of course, a lubricant is applied between the inner vinyl sheets (11) (12).

FIGS. 8-A,B are sections of the reversed state of the present invention as shown in FIGS. 7-A,B, and they represent the insertion stage into the vagina at the reversed state of the margin between the sealing line (2) and the cut line (1) from the outside to the inside.

Here, the lubricant (24) applied between the vinyl sheets (11) (12) of FIG. 7-A has the same effects on the outside of the vinyl sheets (11) (12) of FIGS. 8-A,B when reversed.

Figure 9:
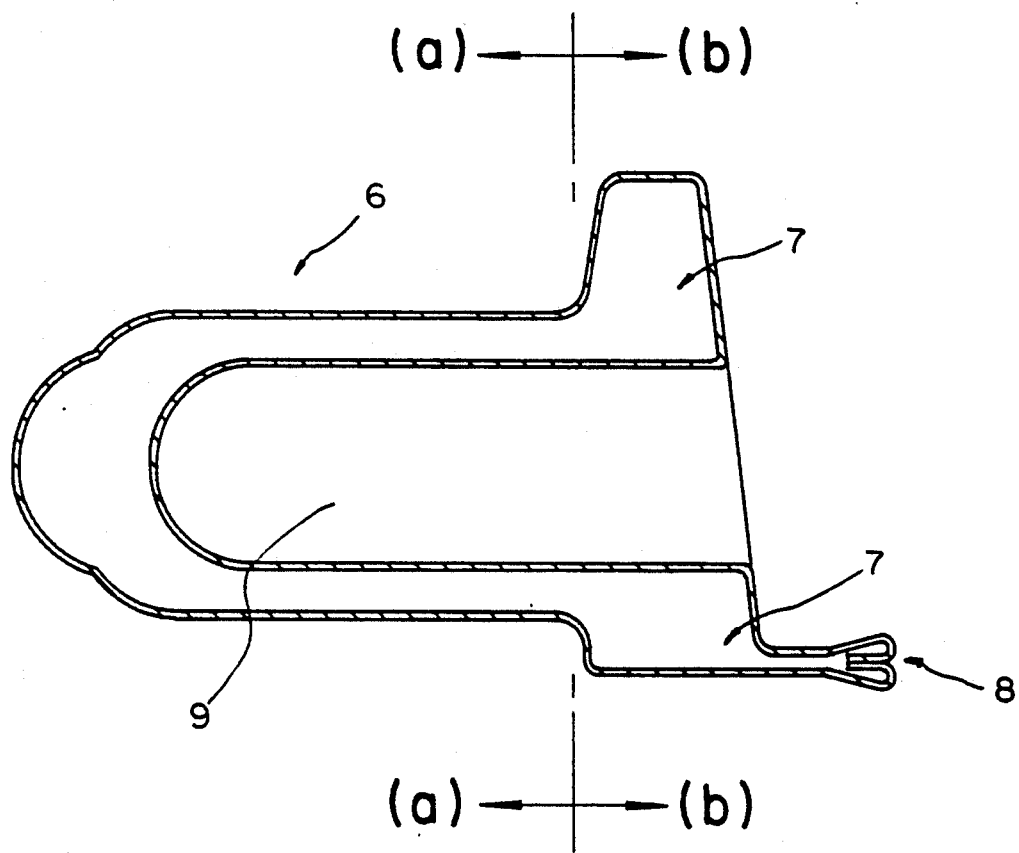
FIG. 9 is a longitudinal side sectional view of the inflated state of the present invention.

FIG. 9 shows another longitudinal section slightly away from the cut line (1) and the sealing line (2) assuming that the penis (9) is inserted into the present invention whether or not reversed, the part (A) corresponds to the insertion part (6) and the part (B) corresponds to the pressure part (7), including the air hole (8).

Figure 10:
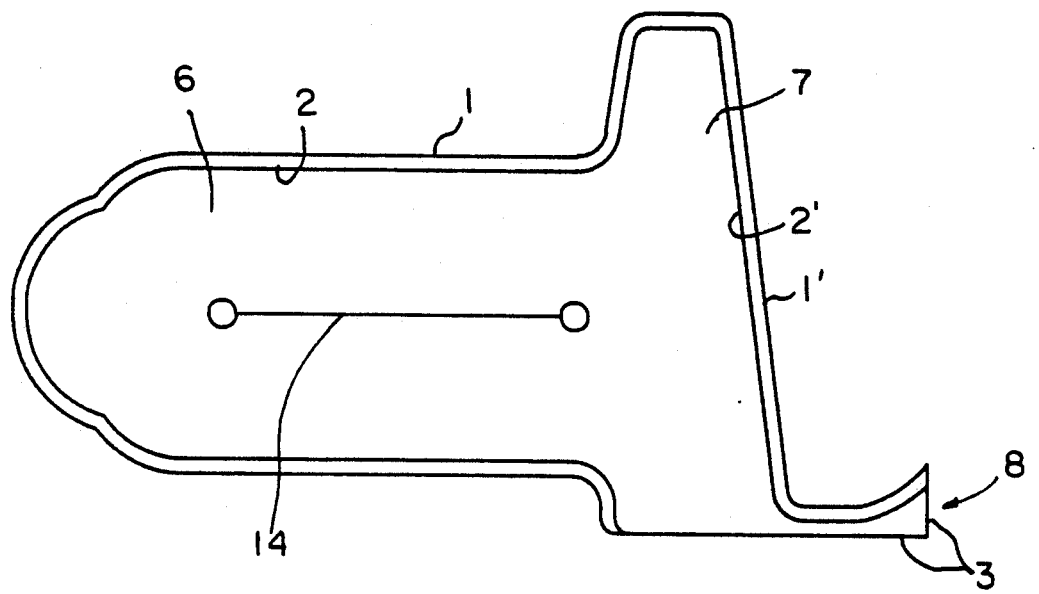
Figure 10:
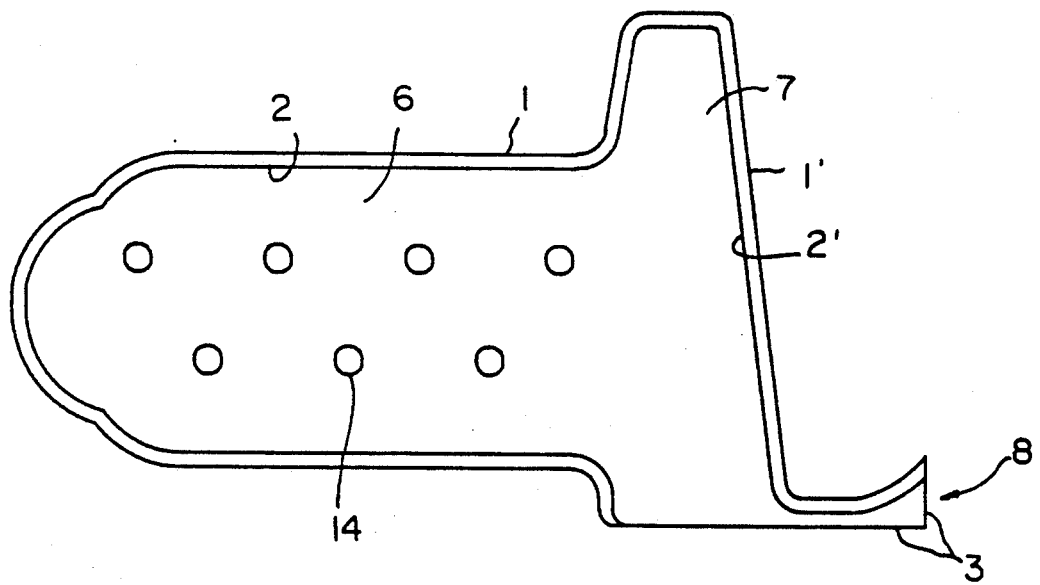

FIGS. 10-A,B show the sealing line forming rugged surface (4) shaped on the insertion part (6). The embodiments of FIG. 2 to FIG. 9 are only air-tight sealing lines (2) (2') preventing the leakage of any air introduced from the air hole (8).

The air spaces between the sealed vinyl sheets (10) (11) (12) (13) are able to solve the problems of a premature ejaculation and small-short complex except for a unrugged state. Therefore, the certain shape of sealing line (14) of an uneven surface is formed in order to achieve enhanced satisfaction.

Plain air-tight sealing lines comprise sealed 4 plys or 2 plys vinyl sheets (10) (11) (12) (13), however the sealing line forming the rugged surface (14) comprises 2 plys vinyl sheets. The said sealing line forming the rugged surface (14) can have an almost infinite variety of forms and shapes of which the sealing line comprises a single straight line as in FIG. 10-A or circular lines as in FIG. 10-B forming a rugged surface by shutting out the air around the circular sealing line.

Figure 11A:
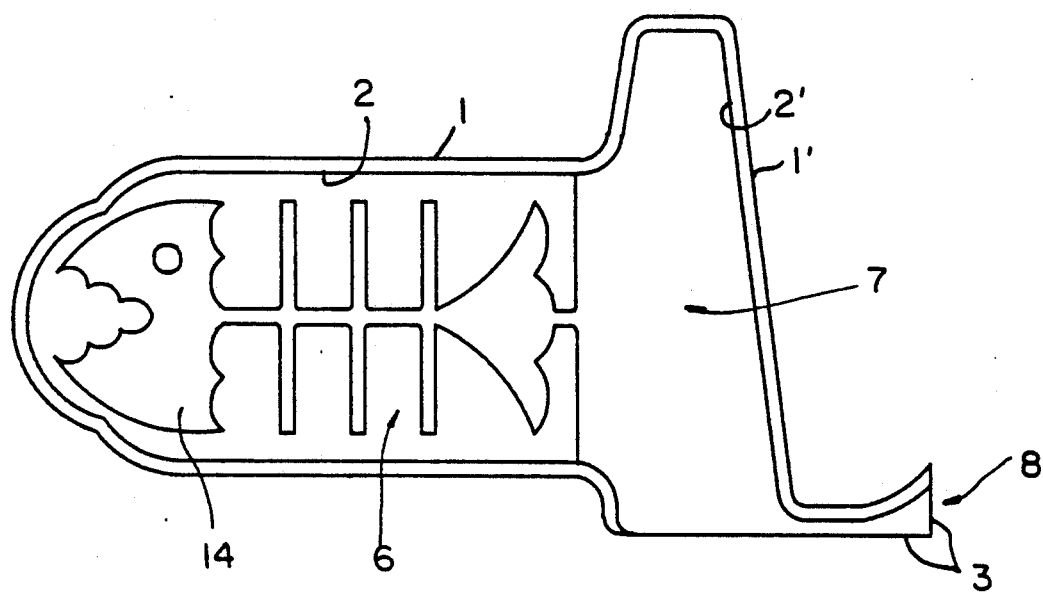
Figure 11B:
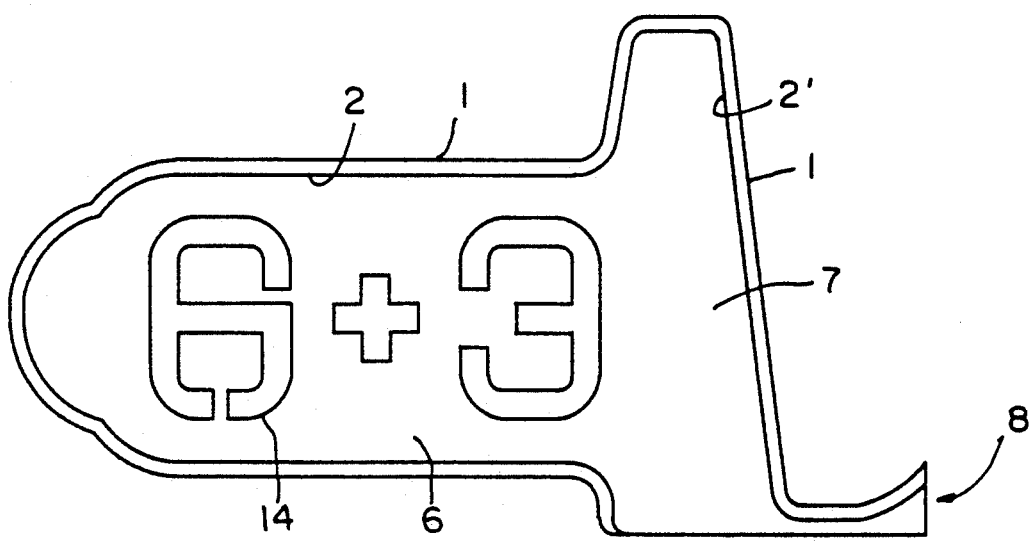

FIG. 11-A is an embodiment showing a fish-shape forming the rugged surface when air is filled in the air space between the pressure part (7) and the insertion part (6) through the air hole and another figure of "6+3" which the air is not inflated due to the sealed enclosure line. In addition, a variety of letters, figures or signs can be applied to create an interesting sealing line forming the rugged surface (14).

FIG. 12-A is a sectional view showing the insertion part (6) inflated to about half after reversing the present invention as in FIG. 10-A, and it has 4 air sacs formed by the sealing line forming the rugged surface (14) as shown in FIG. 10-A. If the rugged sealing line (14) is made by two lines as shown in FIG. 10-A, six air sacs are formed as in FIG. 12-B. Also, the section FIGS. 12-A,B show about a half-inflated state, and the sections of air sacs gradually come near circular form as more air is blown in. The prominence and depression (15) in FIGS. 13-A and B are formed by entirely different processes and structures from the rugged sealing method shown in FIG. 10 to FIG. 12. FIG. 13-A shows the bigger vinyl surface that forms a half-moon figure seen from the side of the circular part which is the prominence and depression (15) of FIG. 13-A by press-forming the 4-plys structures of the present invention. Here, the said 4 ply vinyl sheets (10) (11) (12) (13) are pressed together at one time. FIG. 13-B comprises a two-plys pressure part (7) that is pressed together. FIGS. 14-B and C are the sections showing the prominence and depression (15) of the inserting part (6) made bigger by a bending press as shown in FIG. 13-A, and FIG. 14-A is a section of one vinyl sheet. Here, all the 4 plys comprising the inserting part (6) are folded as in FIG. 14-A, and FIG. 14-A is one section of them. FIG. 14-B shows an inflated state without reversing and three prominence and depression (15) parts formed on both sides centered on the top and bottom cut line (1). Although air is blown in after reversing in order for entering the cut line (1) into inside, the prominence and depression (15) is exposed outside by air pressure and takes the form shown in FIG. 14-C.

FIG. 15 is an embodiment of the partial inflation of the pressure part (7) and the insertion part (6), and the part of the insertion part (6) not allowing any air to be blown in comprises one ply.

Figure 16A:
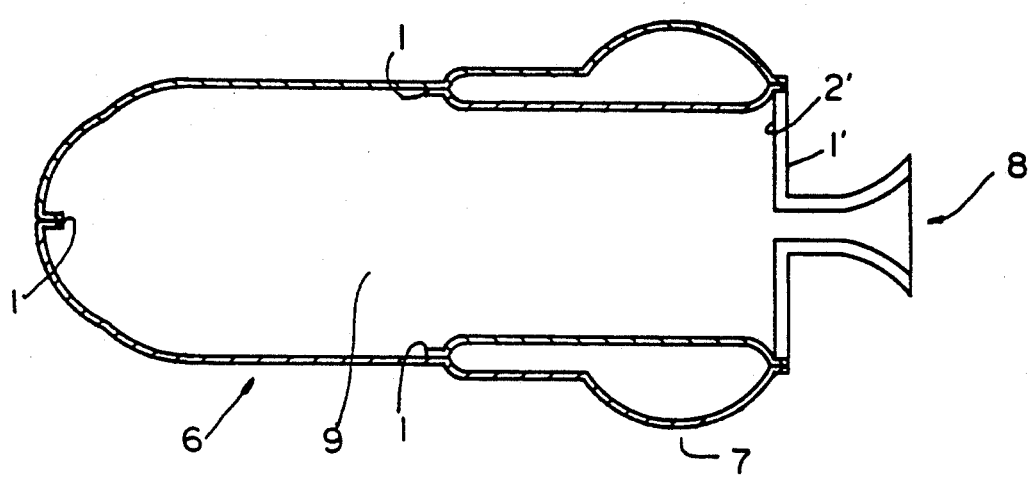
Figure 16B:
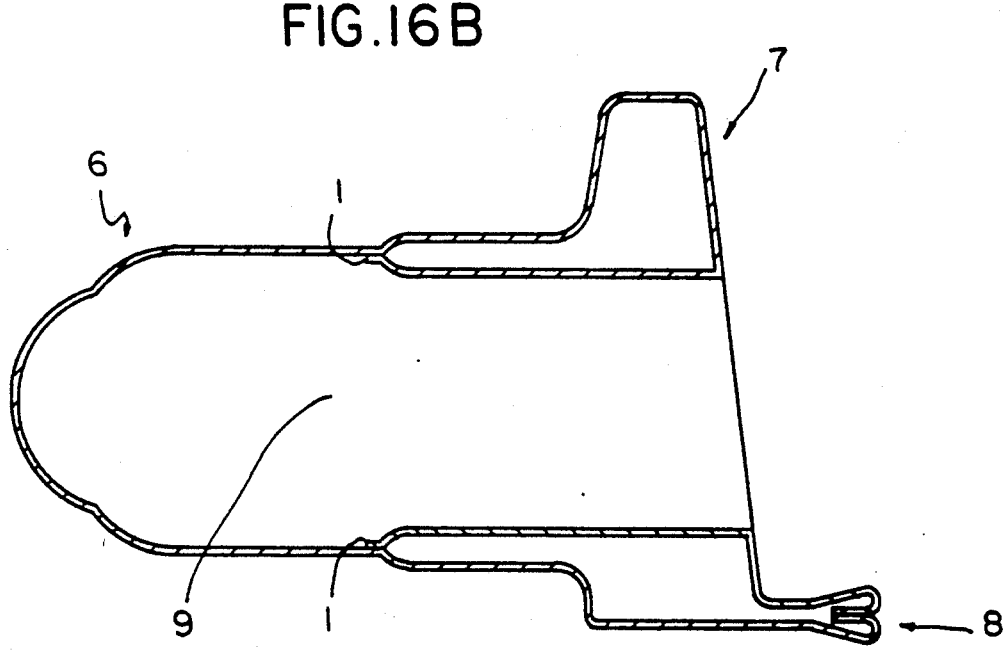

The sections of FIGS. 16-A and B show sections assuming that penis is inserted after inflating the reversed state of FIG. 15.

This is a structure for supplementing the lessening stimulation on penis by means of a full inflation into the whole pressure part and the insertion part.

Figure 17A:
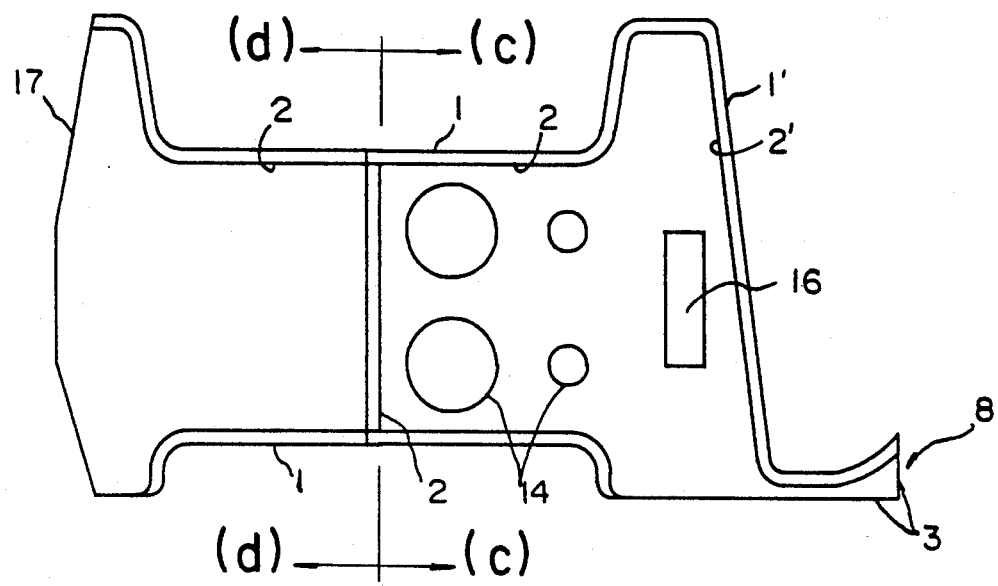
FIG. 17 to FIG. 18 are the embodiments of the present invention used as a sexual device.
Figure 17B:
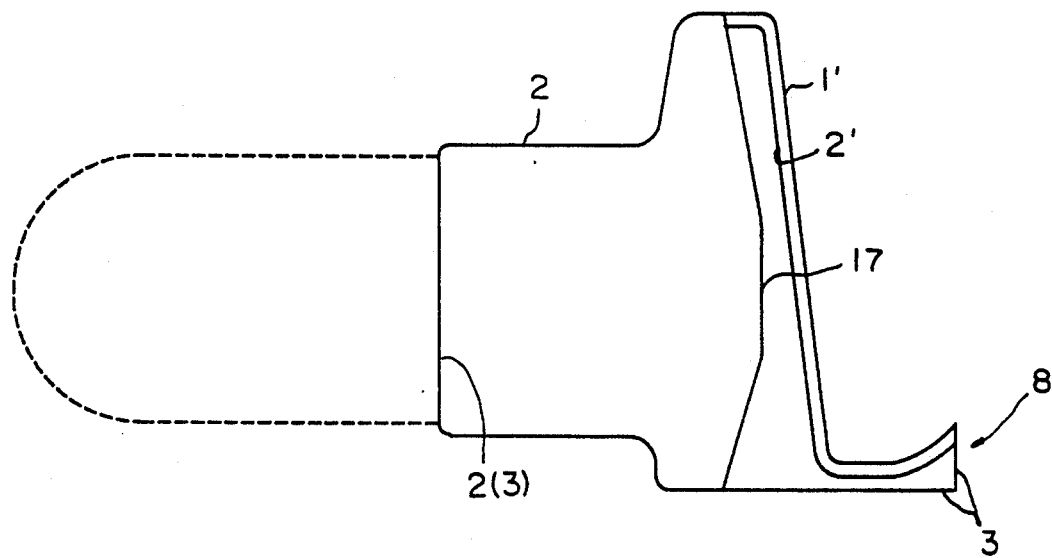

The embodiment of FIGS. 17-A,B is an apparatus devised for achieving only sexual satisfaction without any effect of a condom for an contraception or prevention of venereal disease. FIG. 17-A is a front view of side (C) showing the same structure as the one from FIG. 2 to FIG. 9 centered on the sealing line (2) of the insertion part (6), i.e. one line of the cut lines (1) and the sealing line (2) which are parallel above and below from the center.

A one-ply vinyl sheet cover (17) is used as in FIG. 17-B. FIG. 17-B may be the front view assuming that penis (dotted line) is inserted after the cover (17) is put on. That is to say, the side (C) of FIG. 17-A is made with the same structure as the one from FIG. 2 to FIG. 9, and side (D) is made as a one-ply vinyl sheet to be used as a cover (7). The cover (17) does not slip off during coition because the cover (17) is stuck to the vinyl applied with adhesive after removing tape (16) as shown in FIG. 17-A.

Figure 18A:
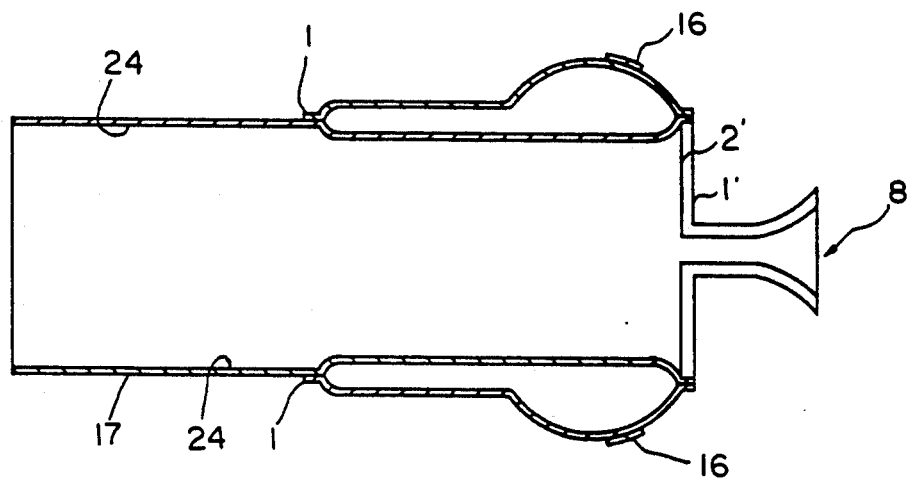
Figure 18B:
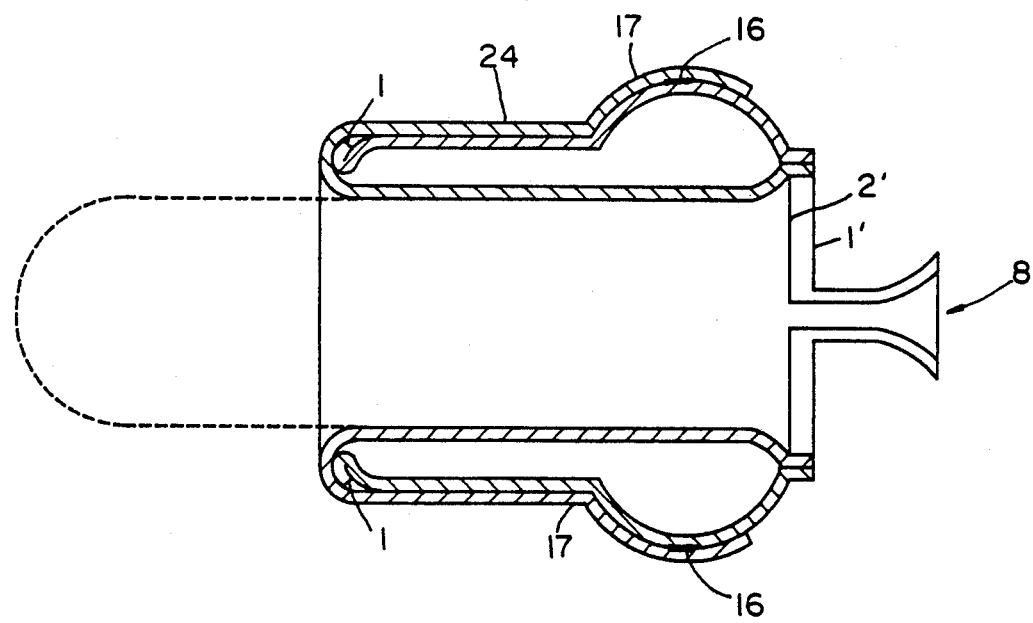

FIG. 18-A is a sectional view prior to reversing and closing of the cover on one side, both sides of which are applied with the lubricant (24). The sectional view of FIG. 18-B shows the state of (shown in dotted line)

inserted into the present invention of which the cover (17) is closed and air is blown in. Also, the cut line (1) appearing outside of FIG. 18-A is folded by bending, as in FIG. 18-B-1, and hidden between the vinyl so that it does not cause any affect on the vagina. When using the present invention, air is inflated into the pressure part (7) and the insertion part (6), and it is closed by a cover (17), and then penis (9) is inserted into it, like putting a ring on a finger.

FIGS. 19-A, B is an embodiment of a sexual apparatus used as a condom for both male and female characterized in a versatile application to both penis and vagina. Part (E) represented in FIG. 19-A is taped with adhesive on the state of FIG. 2-B. Part (F) is formed with only one ply and it has an almost similar type and size cover (17) and also adheres to part (E). The said cover (17) can be used without reversing part (E) and it covers the exposed cut lines by using, not reversing part (E). Here, the cut line (1) of the cover (17) enters inside with the cover (17) itself being reversed.

FIG. 19-B is a section of FIG. 19-A in which the lubricant (24) is applied.

Figure 20A:
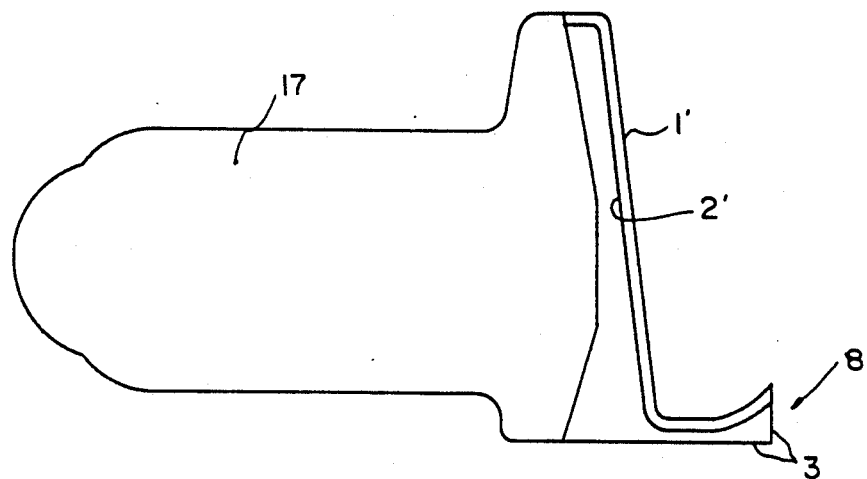
Figure 20B:
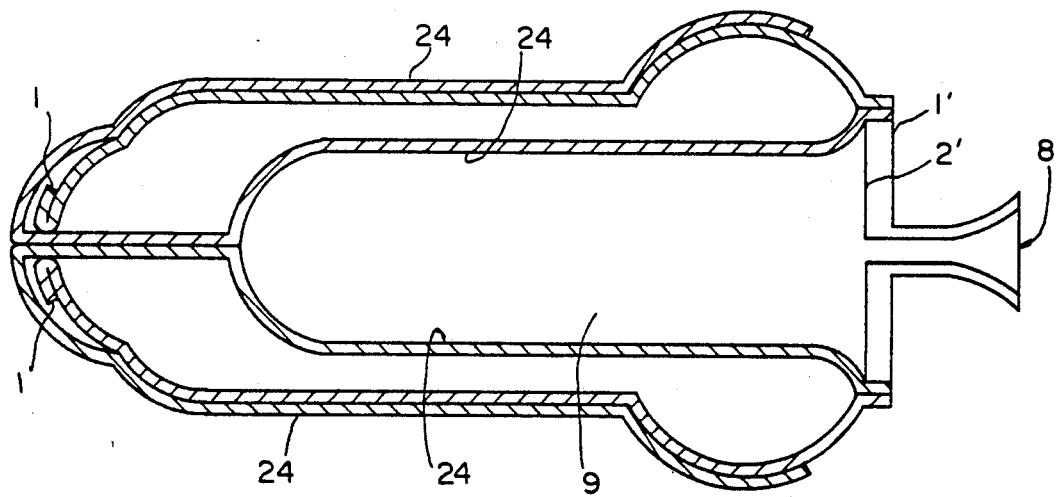

FIG. 20-A is a front view of the closed covering (17), and FIG. 20-B shows a section assuming that an air is blown into the state of FIG. 20-A and penis (9) is inserted in it.

Figure 21:
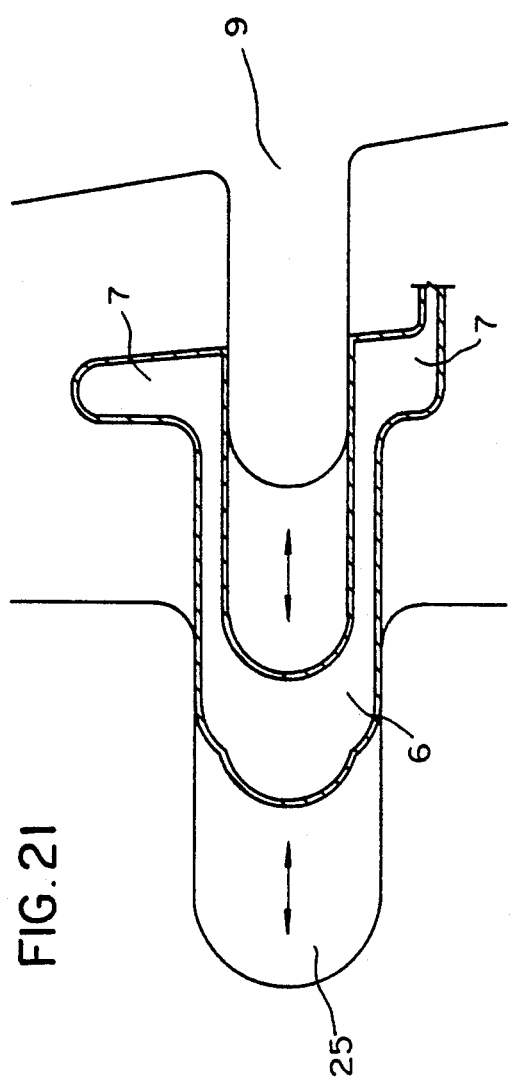

FIG. 21 shows the state of the present invention to be used for penis and vagina and reference numerals (25), (9), (7) and (6) show, vagina, penis, the pressure part and the insertion part respectively.

Figure 22:
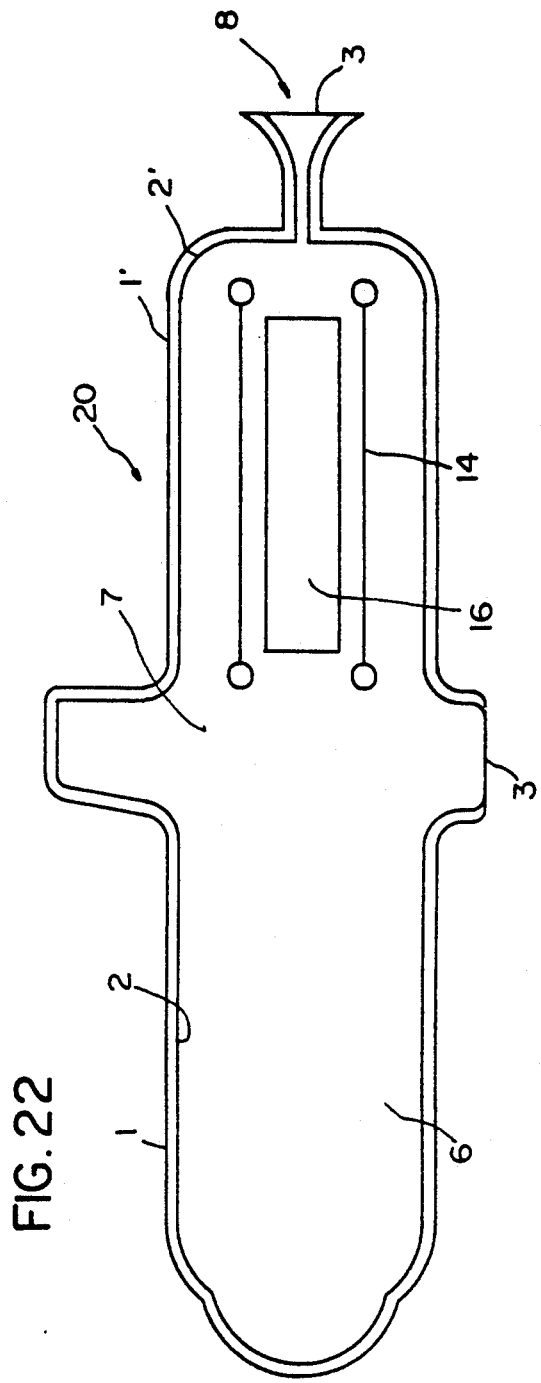
FIG. 22 to FIG. 26 are the embodiment of the present invention used as an artificial penis.

FIG. 22 is a front view showing the embodiment of an artificial penis. The rectangular form represented by reference numeral (16) shows the form of the tape covering the adhesive. The insertion part (6) and the pressure part (7) also have almost same constitution as the one represented in FIG. 2 to FIG. 29.

Figure 23:
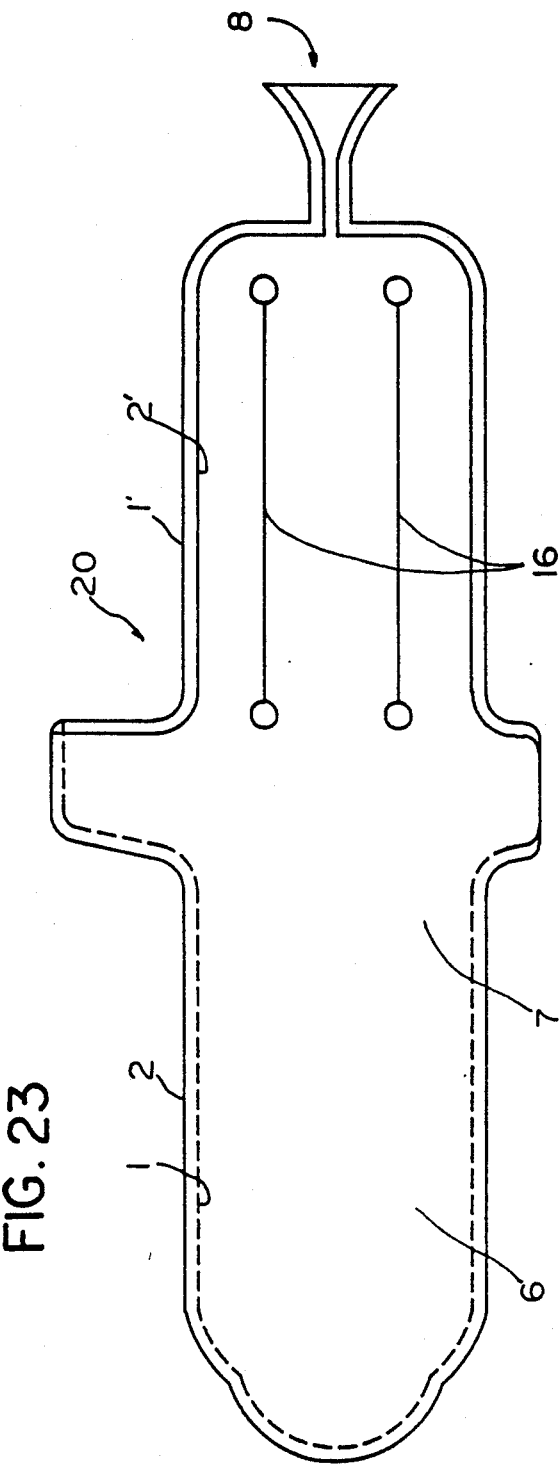

FIG. 23 is a front view of the reversed state of FIG. 22, and the cut line (1) of the insertion part (6) and the pressure part (7) are represented by a dotted line showing the inside of the sealing line (2), and the part adhering to tape (16) does not change its form only when reversed, and only the adhesive tape is not shown positioned inside.

Figure 24:
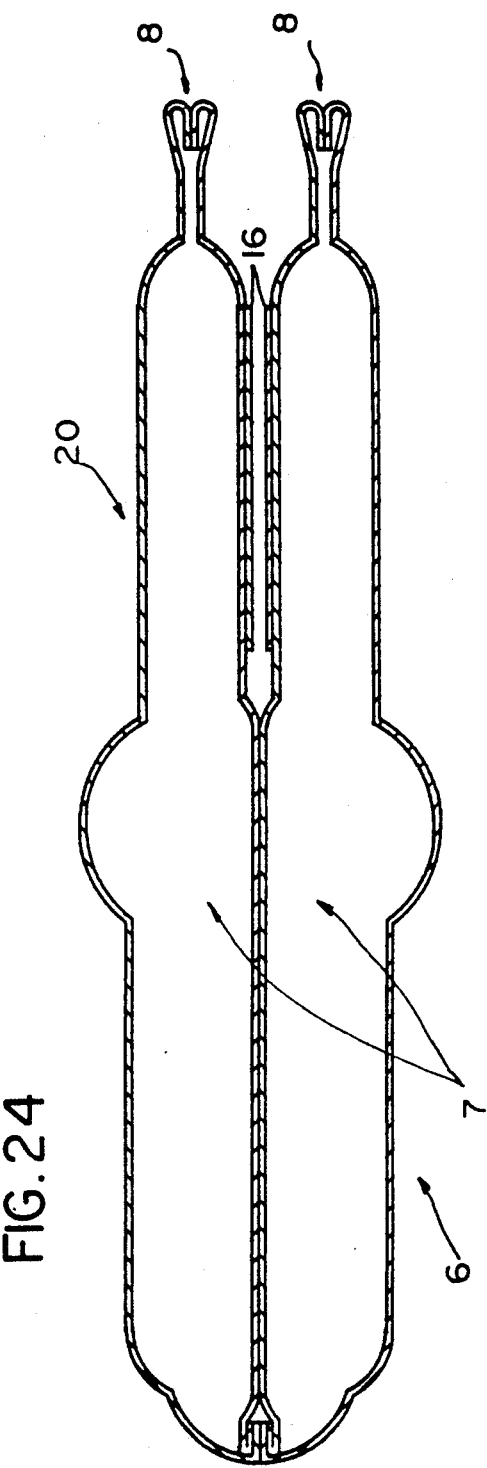

FIG. 24 is a section of the cut line to be symmetrically lengthwise after an inflation as in FIG. 23, and two of the air holes (8) are shown here without any particular reason, but the said two air holes are more advantageous in terms of the manufacturing processes. The long part connected from the pressure part (7) to the air hole (8) shaped like two human legs play the role of a handle.

Figure 25A:
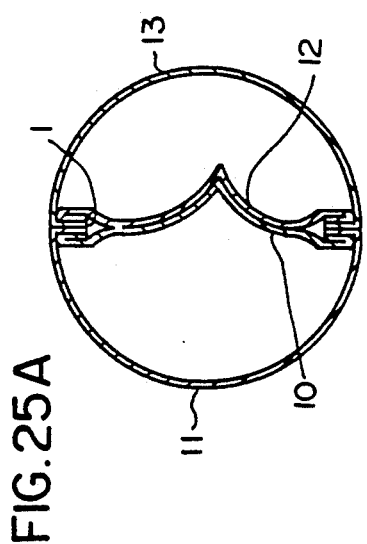
Figure 25B:
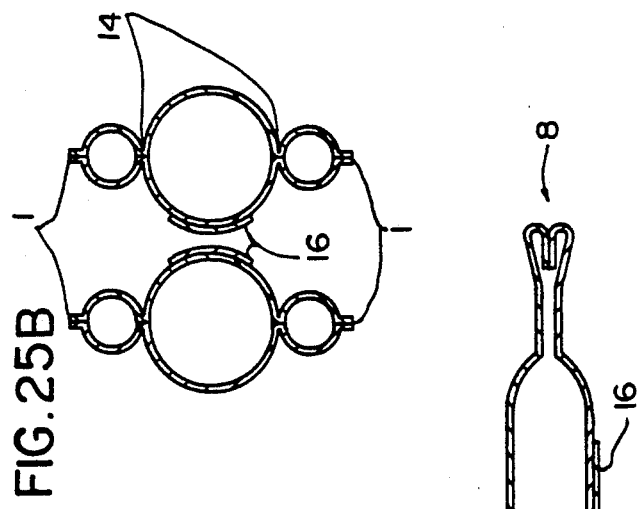

FIGS. 25-A, B show each section of the insertion part (6) and the handle part (20) of FIG. 24.

Figure 26:
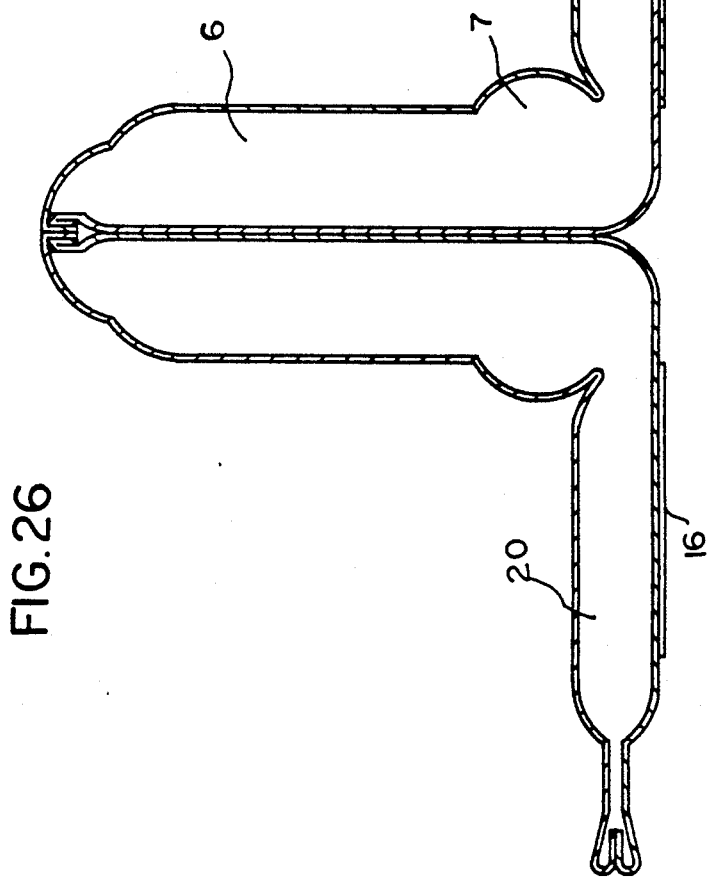

FIG. 26 shows the section of a stretched handle (20) shaped like two human legs in order to affix it to a floor, a chair or a knee. Here, an adhesive is used appearing after removal of the tape (16) from the handle (20) shaped like two legs.

FIGS. 27-A, B is a front view of a sexual device which is also used as a condom having a separable pressure part (7) and insertion part (6). The shape in the front view of the insertion part (6) is similar to that of FIG. 2-B; however air can not be blown in owing to the one-ply composition.

In addition, a one-ply dividing sheet (22) is integrally provided at the position of the pressure part (7), and the pressure part (7) enclosed from the cut-off line (21) marked with a short dotted line in the center of FIG. 27-A to the air hole (8) shows another different form and composition from basic type of the pressure part (7) and the pressure part (7) of the present invention has 4 sealed plys only for the air hole (8) with both the 2 remaining plys sealed. The insertion part (6) and the pressure part (7) are separated along the cut line (21), and the insertion part is placed onto penis by reversing the insertion part after inflating the pressure part (7). Then penis (9) is inserted into the insertion hole (18) of the pressure part (7) as a ring is inserted on the finger. Here, the air hole (8) should be directed toward the feet of a male, and four inner diameter controlling parts (19) having a half-circle form around the insertion hole (18) of penis in order to assure a desirable tightness without causing any breakage around the insertion hole (18). The pressure part (7) to be mentioned later has the same constitution and operational effect as that of FIG. 27-A.

FIG. 27-B is a section seen symmetrically assuming that the pressure part (7) is inflated.

FIG. 28-A is an embodiment of a cone shaped hat of which the entering part is wide enough to be reversed with ease and is easy to put on. It is like wearing a big cone shaped hat on the head. It enables a male to put the inflated pressure part (7) over his penis (9) inserted with a cone shaped insertion part (6). The appearance, after putting it on, resembles that of a folded umbrella held by its holding band. The inserting part (6) comprises a one-ply vinyl sheet; therefore it can not be inflated with air. However, the peculiar folded raffles are able to create significant effects, such as premature ejaculation of a male simultaneously with heightening the sexual sensation of a female. Also, the long length of the cutting part (1) and the sealing part (2) of the insertion part (6) in the manufacturing process are substantially decreased. The line represented by the reference numeral (3) shows the folded line having two ply from the one ply prior to its folding. FIG. 28-B shows a section of the circular periphery of the entering part of the insertion part (6) after the insertion part (6) and the pressure part (7) are separated by a dotted line (20), and also the pressure part (7) is inflated.

Figure 29A:
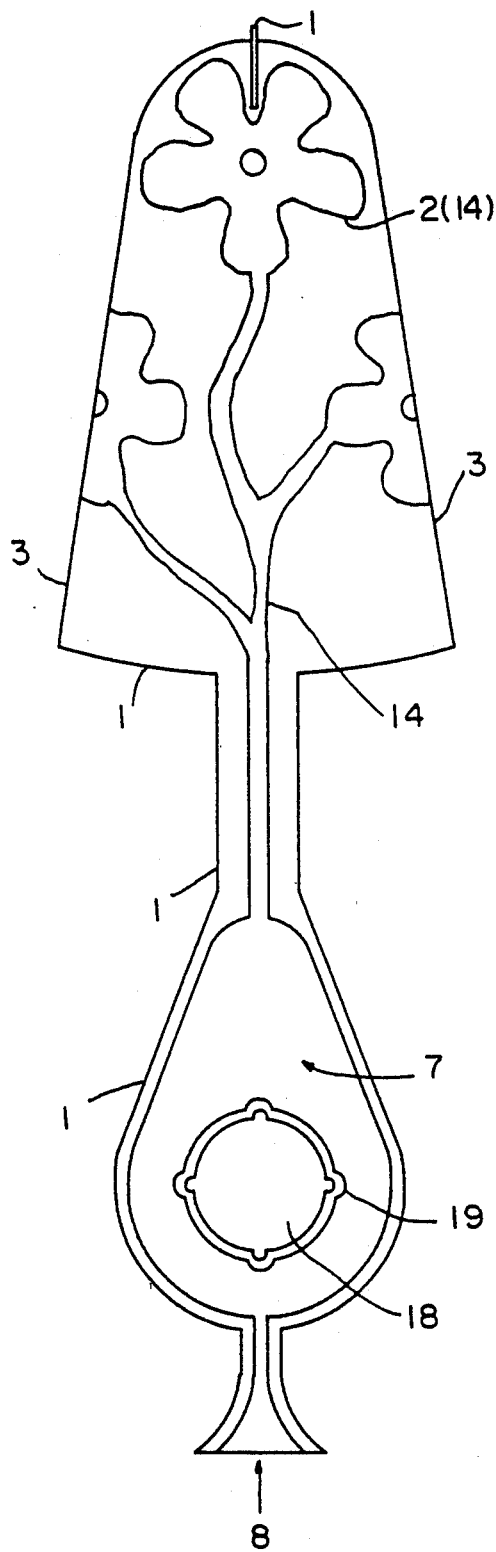
FIG. 29 to FIG. 30 are the embodiment showing the formation of the sealing line forming a certain shape as in FIG. 28-A to FIG. 28-B.
Figure 29B:
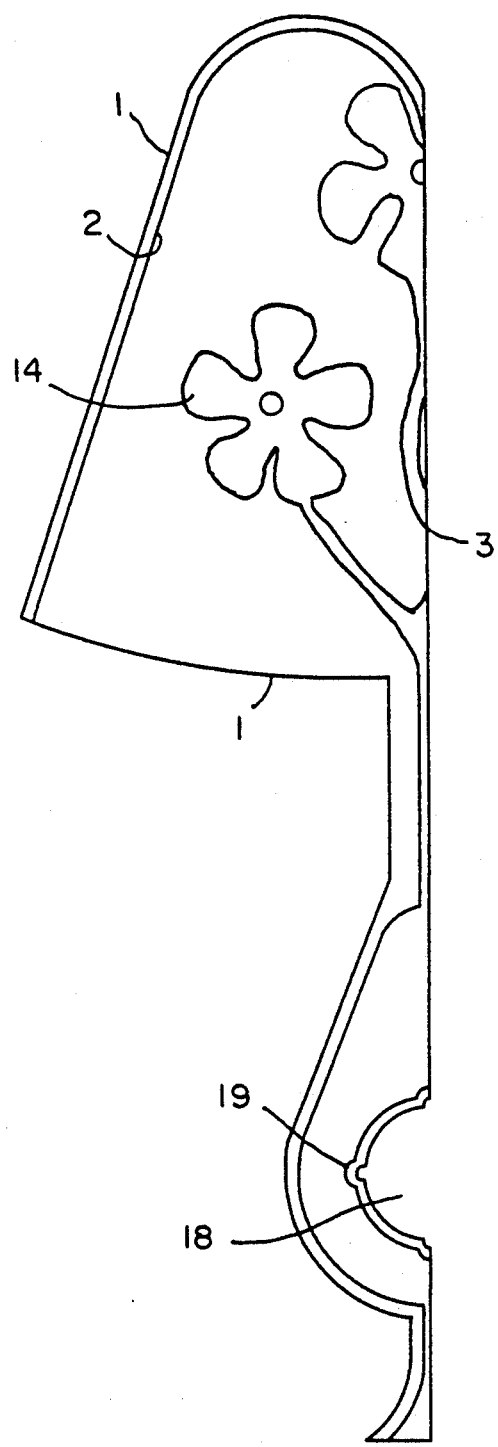
Figure 30A:
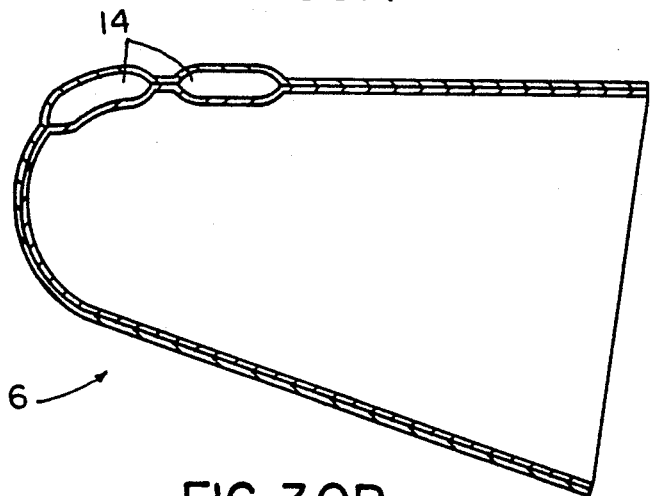
Figure 30B:
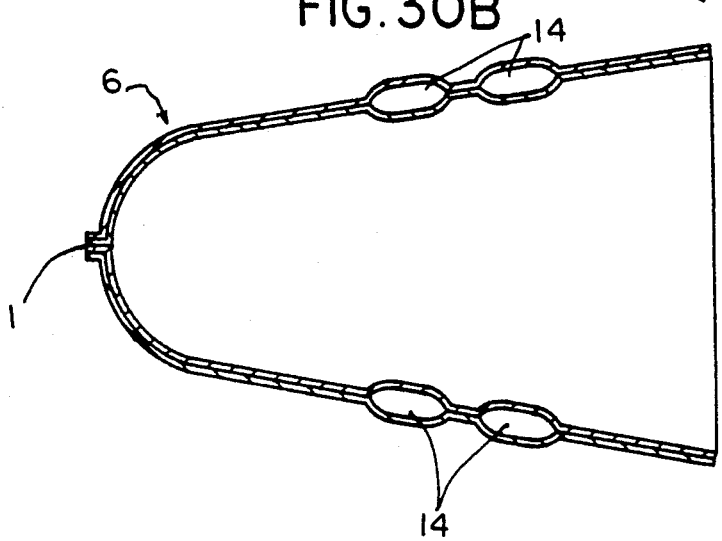
Figure 30C:
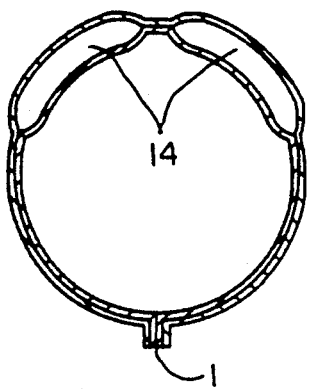
Figure 30D:
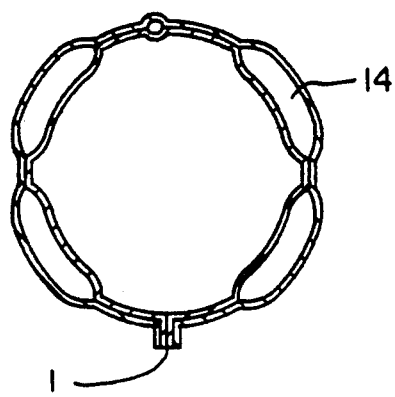

FIGS. 29-A, B is just the same as the embodiment of FIGS. 28-A, B except for the two-ply insertion part (6) formed with a flower shape inflatable rugged surface in the sealing line (14).

FIG. 29-B is a front view of a pressure part (7) folded lengthwise symmetrically with that of FIG. 29-A.

FIGS. 30-A to D is a section of the state of the present invention inflated into the insertion part of FIG. 29, of which only the flower-shape is inflated.

Figure 31:
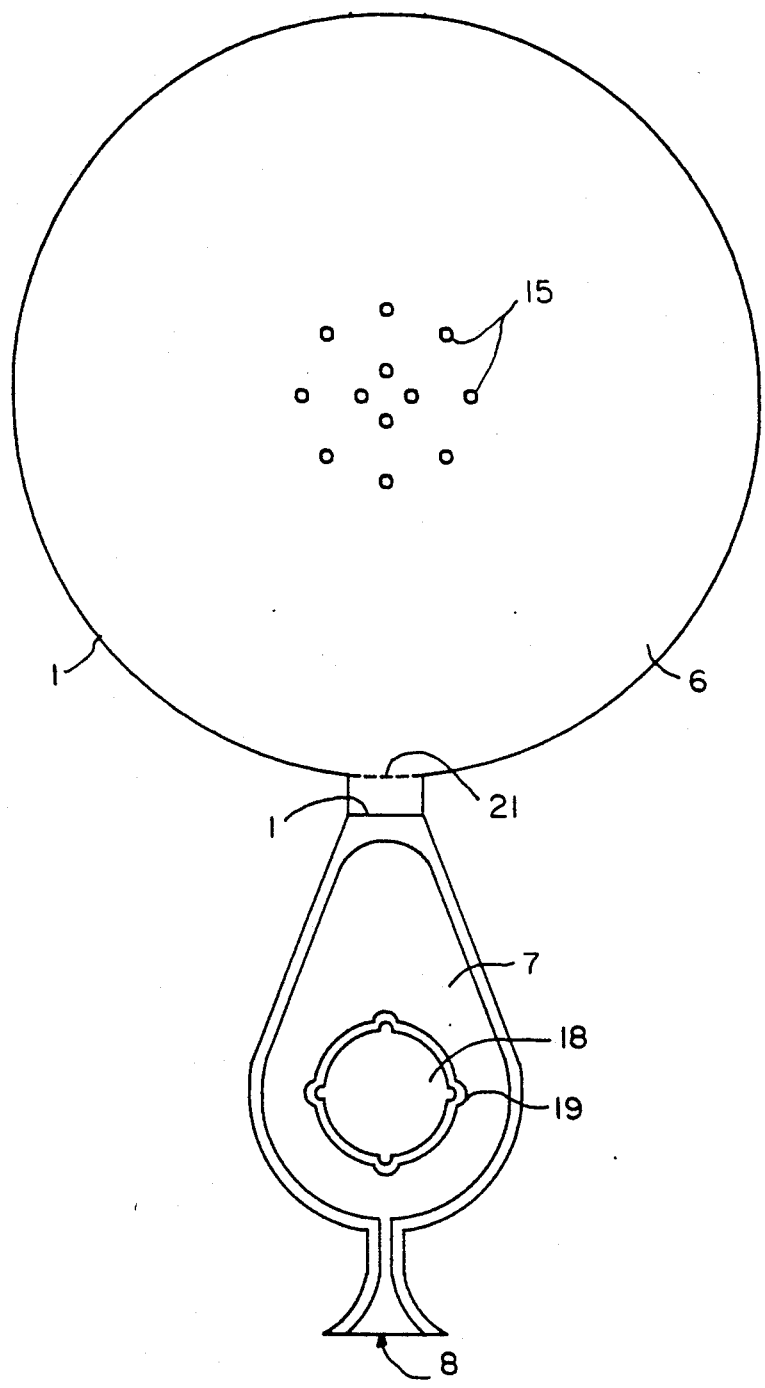
FIG. 31-A to FIG. 31-B are the embodiments showing the state of the circular formation of the insertion part of the present invention.
Figure 31B:
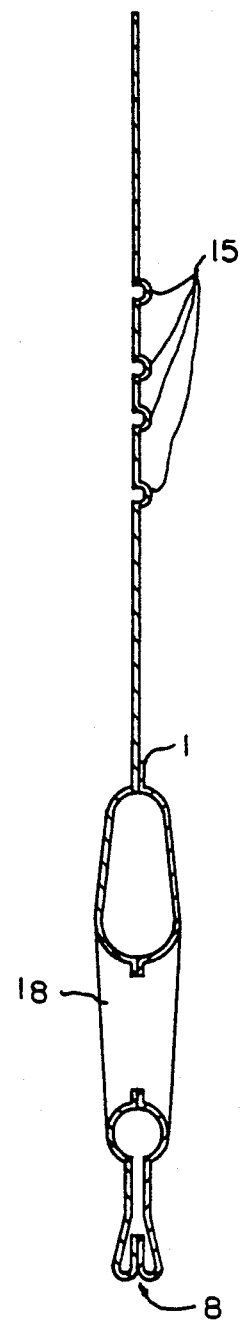

FIG. 31 is an embodiment of a circular one-ply vinyl sheet of the insertion part (6). The two plys of insertion part (6) integrated with the pressure part (7) by sealing in order to be inflated.

FIG. 31-B shows a section of the embodiment symmetrically cut of FIG. 31-A. After putting on the device, more creasings and foldings appear than at the cone shaped insertion part shown in FIGS. 28-A, B. The prominence and depression (15) formed in the center of the insertion part (6) helps to find the center of a circular insertion part (6) as mentioned in FIG. 13.

Figure 32:
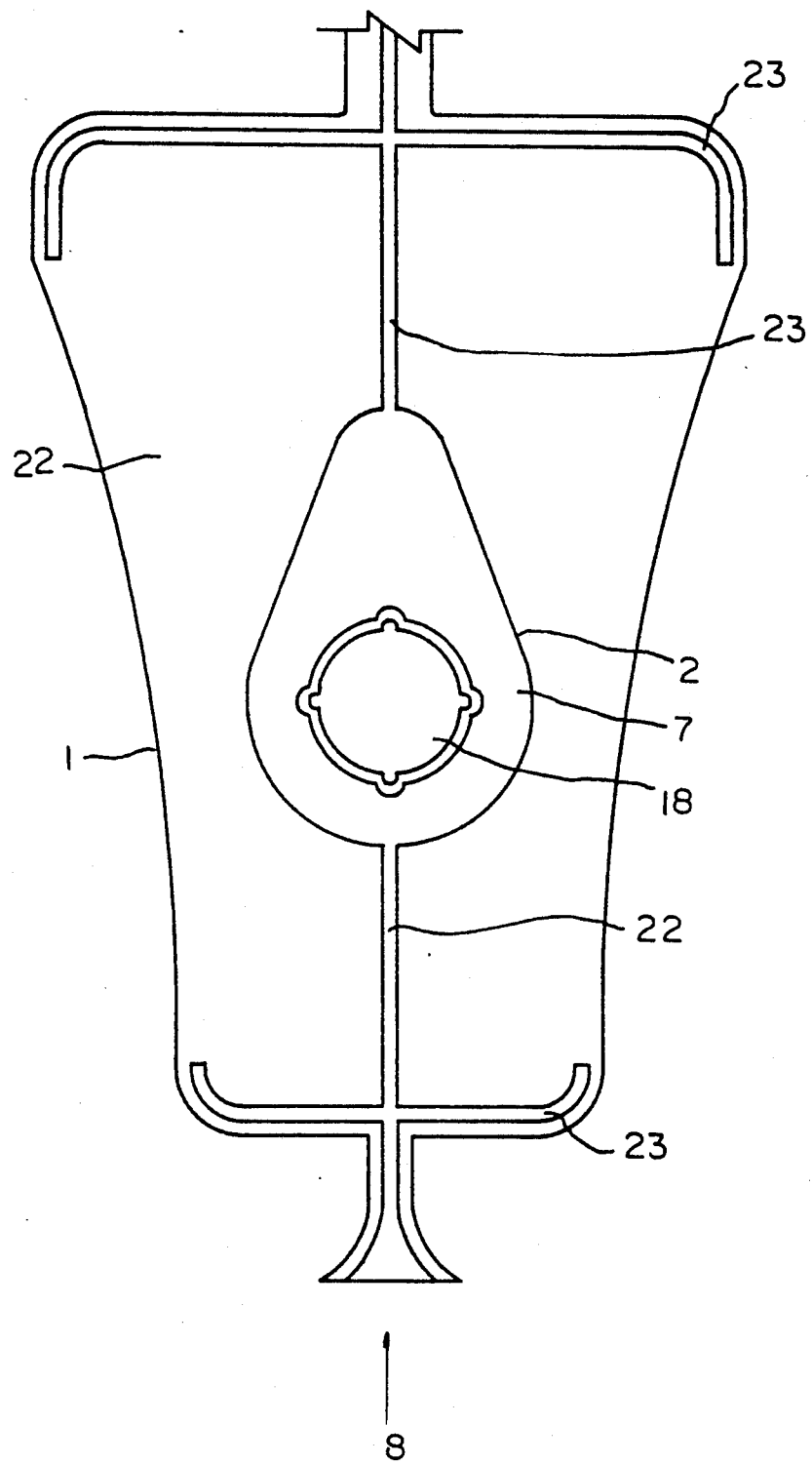
FIG. 32 is an embodiment of the state forming a dividing sheet in the present invention.

FIG. 32 is a plane view provided with a dividing sheet for the present invention, and the dividing sheet (22) comprising wide two-ply vinyl sheets around the pressure part (7) can avoid a direct contact with the periphery of penis with a better assurance than the conventional condom or the above embodiment, in order to achieve a better effect for contraception and prevention of various venereal diseases, and in particular the pain arising form the intense rubbing and pressing on the contacting parts of the public bones of male and female can be relieved by this wide and slippery dividing sheet (22). This dividing sheet (22) is not only formed at the pressure part (7) in FIG. 32, but is also connected to the cut part represented by reference numeral (1') in FIG. 2-B or connected directly to the insertion part (6) as in FIG. 27-A.

The dividing sheet (22) is made of a wide and thin vinyl; therefore, it can be supported by the air passage part or air pillar (23) in order to prevent accidental folding or flapping.

Of course, the present invention can be worn over the conventional condom with satisfactory effects.

I claim:

1. An inflatable multipurpose sexual device which can be used as a condom, said device comprising:
    an inner sheet sized and shaped to fit around a penis;
    an outer sheet, at least partially surrounding and sealingly joined to said inner sheet at a sealing line, said inner and outer sheets defining an air inflation chamber, said chamber, when inflated, comprising a means for separating said inner and outer sheets except at said sealing line; and
    an air inflation valve connected to said chamber for inflating said chamber.

2. The device according to claim 1, wherein said inner and outer sheets comprise a means for defining both an insertion part and adjacent to said insertion part, a pressure part, said insertion part having a diameter capable of being inserted into a vagina and said pressure part having a larger diameter than said insertion part.

3. The device according to claim 2, wherein said inner sheet comprises a single sheet folded and sealed to itself so as to surround said penis, said outer sheet folded and sealed to itself so as to surround said inner sheet, said outer sheet and said inner sheet are sealingly joined to each other along a sealing line comprising said air inflation chamber.

4. The device according to claim 2, further including at least one additional sealing point between said inner and outer sheets forming at least one depression in an external surface of said outer sheet when said air chamber is filled with air.

5. The device according to claim 4, wherein said at least one additional sealing point is located on said pressure part.

6. The device according to claim 4, wherein said at least one additional sealing point is located on said insertion part.

7. The device according to claim 2, further including a cover for covering said insertion part, said cover joined to said insertion part at a front edge of said insertion part.

8. The device according to claim 7, wherein said cover comprises an extended portion of said inner sheet sealed to itself forming a cover which can be folded back over said insertion part.

9. The device according to claim 2, wherein said pressure part further includes means for forming an integral handle.

10. An inflatable multipurpose sexual device which can be used as a condom, said device comprising:
    an inner sheet sized and shaped to fit around a penis;
    an outer sheet, only partially surrounding but completely sealingly joined to said inner sheet along a sealing line, said inner and outer sheets defining an air inflation chamber, said chamber, when inflated, comprising a means for separating said inner and outer sheets except at said sealing line; and
    an air inflation valve connected to said chamber for providing inflation air to said chamber.

11. The device according to claim 10, wherein said inner and outer sheets comprise a means for defining both an insertion part and an adjacent pressure part, said insertion part having a diameter capable of being inserted into a vagina and said pressure part having a larger diameter than said insertion part, said insertion part at least partially comprised of a portion of said inner sheet not surrounded by said outer sheet.

12. An inflatable multipurpose sexual device which can be used as a condom, said device comprising:
    an inner sheet sized and shaped to fit around a penis;
    an outer sheet, at least partially surrounding and sealingly joined to said inner sheet at a sealing line with an aperture permitting entry of said penis, said inner and outer sheets defining an air inflation chamber, said chamber, when inflated, comprising a means for separating said inner and outer sheets except at said sealing line, wherein said inner and outer sheets comprise a means for defining both an insertion part and, adjacent to said insertion part, a pressure part, said insertion part having a diameter capable of being inserted into a vagina and said pressure part having a larger diameter than said insertion part;
    a dividing sheet means for detachably connecting said insertion part to said pressure part; and
    an air inflation valve connected to said chamber for inflating said chamber.

13. The device according to claim 12, wherein said pressure part further including a means for controlling the size of said aperture.

14. The device according to claim 12, wherein said insertion part comprises a cone shaped hat.

15. The device according to claim 14, wherein at least one sealing line is present on an outer surface of said outer sheet.

* * * * *